(12) United States Patent
Alarcon et al.

(10) Patent No.: US 7,787,923 B2
(45) Date of Patent: *Aug. 31, 2010

(54) FIBER OPTIC DEVICE FOR SENSING ANALYTES AND METHOD OF MAKING SAME

(75) Inventors: Javier Alarcon, Durham, NC (US); Kristin Weidemaier, Raleigh, NC (US); Terry J. Amis, Cary, NC (US); John D. DeNuzzio, Monkton, MD (US); Christopher C. Herdman, Chappaqua, NY (US); Ross W. Jacobson, Hillsborough, NC (US); J. Bruce Pitner, Durham, NC (US); Douglas B. Sherman, Durham, NC (US); Steven Keith, Chapel Hill, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1232 days.

This patent is subject to a terminal disclaimer.

(21) Appl. No.: 10/967,220

(22) Filed: Oct. 19, 2004

(65) Prior Publication Data

US 2005/0113658 A1    May 26, 2005

Related U.S. Application Data

(63) Continuation-in-part of application No. 10/721,797, filed on Nov. 26, 2003, now Pat. No. 7,496,392.

(51) Int. Cl.
A61B 5/145 (2006.01)

(52) U.S. Cl. .................. 600/316; 600/317; 600/342

(58) Field of Classification Search .............. 600/317, 600/322, 341, 342
See application file for complete search history.

(56) References Cited

U.S. PATENT DOCUMENTS

| 4,515,584 A | 5/1985 | Abe et al. |
| 4,526,569 A | 7/1985 | Bernardi |

(Continued)

FOREIGN PATENT DOCUMENTS

EP    0481740    4/1992

(Continued)

OTHER PUBLICATIONS

Ballerstadt et al., Competitive-Binding Assay Method Based on Fluorescence Quenching of Ligands Held in Close Proximity . . . , Anal. Chim. Acta 345, 1997, pp. 203-212.

(Continued)

*Primary Examiner*—Eric F Winakur
*Assistant Examiner*—Etsub D Berhanu
(74) *Attorney, Agent, or Firm*—Morgan, Lewis & Bockius LLP

(57) ABSTRACT

A device for sensing analyte concentration, and in particular glucose concentration, in vivo or in vitro is disclosed. A sensing element is attached to the distal end of an optical conduit, and comprises at least one binding protein adapted to bind with at least one target analyte. The sensing element further comprises at least one reporter group that undergoes a luminescence change with changing analyte concentrations. Optionally, the optical conduit and sensing element may be housed within a cannulated bevel.

35 Claims, 11 Drawing Sheets

U.S. PATENT DOCUMENTS

| | | | |
|---|---|---|---|
| 4,548,907 A | 10/1985 | Seitz et al. | |
| 4,907,857 A | 3/1990 | Giuliani et al. | |
| 4,925,268 A | 5/1990 | Iyer et al. | |
| 4,981,779 A | 1/1991 | Wagner | |
| 5,001,054 A | 3/1991 | Wagner | |
| 5,062,841 A | 11/1991 | Siegel | |
| 5,104,959 A * | 4/1992 | Hess et al. | 528/79 |
| 5,127,405 A | 7/1992 | Alcala et al. | |
| 5,140,366 A | 8/1992 | Komives et al. | |
| 5,143,066 A * | 9/1992 | Komives et al. | 600/317 |
| 5,154,890 A | 10/1992 | Mauze et al. | |
| 5,219,527 A | 6/1993 | Hui et al. | |
| 5,298,022 A | 3/1994 | Bernardi | |
| 5,341,805 A | 8/1994 | Stavridi et al. | |
| 5,342,789 A | 8/1994 | Chick et al. | |
| 5,377,676 A | 1/1995 | Vari et al. | |
| 5,496,997 A | 3/1996 | Pope | |
| 5,552,272 A | 9/1996 | Bogart | |
| 5,569,186 A | 10/1996 | Lord et al. | |
| 5,569,911 A | 10/1996 | Tomlinson et al. | |
| 5,605,152 A | 2/1997 | Slate et al. | |
| 5,626,134 A | 5/1997 | Zuckerman | |
| 5,628,310 A | 5/1997 | Rao et al. | |
| 5,700,897 A | 12/1997 | Klainer et al. | |
| 5,747,349 A | 5/1998 | Van Den Engh et al. | |
| 5,800,420 A | 9/1998 | Gross et al. | |
| 5,807,375 A | 9/1998 | Gross et al. | |
| 5,820,622 A | 10/1998 | Gross et al. | |
| 5,866,433 A | 2/1999 | Schalkhammer et al. | |
| 5,900,215 A | 5/1999 | Seifert et al. | |
| 5,946,083 A | 8/1999 | Melendez et al. | |
| 6,024,923 A | 2/2000 | Melendez et al. | |
| 6,040,194 A | 3/2000 | Chick et al. | |
| 6,045,756 A | 4/2000 | Carr et al. | |
| 6,081,736 A | 6/2000 | Colvin et al. | |
| 6,111,248 A | 8/2000 | Melendez et al. | |
| 6,157,442 A | 12/2000 | Raskas | |
| 6,191,847 B1 | 2/2001 | Melendez et al. | |
| 6,197,257 B1 | 3/2001 | Raskas et al. | |
| 6,197,534 B1 | 3/2001 | Lakowicz et al. | |
| 6,256,522 B1 | 7/2001 | Schultz | |
| 6,277,627 B1 | 8/2001 | Hellinga | |
| 6,285,807 B1 | 9/2001 | Walt et al. | |
| 6,304,766 B1 | 10/2001 | Colvin | |
| 6,330,464 B1 | 12/2001 | Colvin et al. | |
| 6,432,723 B1 | 8/2002 | Plaxco et al. | |
| 6,512,939 B1 | 1/2003 | Colvin et al. | |
| 6,535,753 B1 | 3/2003 | Raskas | |
| 6,544,212 B2 | 4/2003 | Galley et al. | |
| 6,558,351 B1 | 5/2003 | Steil et al. | |
| 6,589,229 B1 | 7/2003 | Connelly et al. | |
| 6,673,596 B1 | 1/2004 | Sayler et al. | |
| 6,704,587 B1 | 3/2004 | Kumar et al. | |
| 6,875,195 B2 | 4/2005 | Choi | |
| 6,977,180 B2 | 12/2005 | Hellinga et al. | |
| 2002/0016535 A1 | 2/2002 | Martin et al. | |
| 2002/0026108 A1 | 2/2002 | Colvin | |
| 2002/0032374 A1* | 3/2002 | Holker et al. | 600/373 |
| 2002/0043651 A1 | 4/2002 | Darrow et al. | |
| 2002/0058863 A1 | 5/2002 | Petersson et al. | |
| 2002/0193672 A1 | 12/2002 | Walsh et al. | |
| 2003/0130167 A1 | 7/2003 | Pitner et al. | |
| 2003/0130569 A1 | 7/2003 | Raskas | |
| 2003/0134346 A1 | 7/2003 | Amiss et al. | |
| 2003/0135333 A1 | 7/2003 | Aceti et al. | |
| 2003/0153026 A1 | 8/2003 | Alarcon et al. | |
| 2003/0232383 A1 | 12/2003 | Daunert et al. | |
| 2004/0092893 A1* | 5/2004 | Haider et al. | 604/272 |
| 2004/0152622 A1 | 8/2004 | Keith et al. | |
| 2004/0234962 A1 | 11/2004 | Alarcon et al. | |
| 2005/0014290 A1 | 1/2005 | Hsieh et al. | |
| 2005/0113657 A1 | 5/2005 | Alarcon et al. | |
| 2005/0148003 A1 | 7/2005 | Keith et al. | |
| 2005/0192557 A1 | 9/2005 | Brauker et al. | |
| 2005/0261561 A1 | 11/2005 | Jones et al. | |
| 2006/0024358 A1 | 2/2006 | Santini et al. | |

FOREIGN PATENT DOCUMENTS

| | | |
|---|---|---|
| WO | WO 00/74763 | 12/2000 |
| WO | WO 03/060464 | 7/2003 |
| WO | WO 03/071930 | 9/2003 |
| WO | WO 2004/044557 | 5/2004 |
| WO | WO 2004/101769 | 11/2004 |

OTHER PUBLICATIONS

Blair et al., Fiber Optic Sensor for Ca2+ Based on an Induced Change in the Conformation of the Protein Calmodulin, Anal. Chem., 66, 1994, pp. 300-302.

De Lorimier et al., Construction of a Fluorescent Biosensor Family, Protein Science, 11, 2002, pp. 2655-2675.

Dwyer et al., Periplasmic Binding Proteins: a versatile superfamily for protein engineering, Current Opinion in Structural Biology, 14, 2004, pp. 495-504.

Ge et al., Dual-Labeled Glucose Binding Protein for Ratiometric Measurements of Glucose, Anal. Chem., vol. 76, No. 5, 2004, 1403-1410.

Gilardi et al., Engineering the Maltose Binding Protein for Reagentless Fluorescence Sensing, Anal. Chem., 66, No. 21, 1994, pp. 3840-3847.

Hellinga et al., Protein Engineering and the Development of Generic Biosensors, Tibtech, vol. 16, 1998, pp. 183-189.

Piszczek et al., Conformational Stability and Domain Coupling in D-glucose/D-galactose-binding protein from *Escherichia coli*, Biochem. J., 381, 2004, pp. 97-103.

Ross et al., Temperature Measurement in Microfluidic Systems Using a Temperature-Dependent Fluorescent Dye, Anal. Chem., 73, 2001, pp. 4117-4123.

Russell et al., A Fluorescence-Based Glucose Biosensor Using Concanavalin A and Dextran Encapsulated in a Poly(ethylene glycol) Hydrogel, Anal. Chem., 71, 1999, pp. 3126-3132.

Salins et al., A Novel Reagentless Sensing System for Measuring Glucose Based on the Galactose-Glucose-Binding Protein, Anal. Biochem., 294, 2001, pp. 19-26.

Shilton et al., Conformational Changes of Three Periplasmic Receptors for Bacterial Chemotaxis and Transport: the Maltose-, . . . , J. Mol. Biol., 264, 1996, pp. 350-363.

Smart et al., Some Advances in Fluorometric Techniques for Water Tracing, Environmental Monitoring and Assessment, 53, 1998, pp. 305-320.

Tolosa et al., Glucose Sensor for Low-Cost Lifetime-Based Sensing Using a Genetically Engineered Protein, Anal. Biochem., 267, 1999, pp. 114-120.

Turner Designs Hydrocarbon Instruments: "10-AU-005-CE Field Fluorometer" (online), Oct. 11, 2004, pp. 1-8 (product brochure).

International Preliminary Report on Patentability for PCT/US2005/037614, dated Apr. 24, 2007.

International Preliminary Report on Patentability for PCT/US2005/037615, dated Apr. 24, 2007.

Rosenzweig, Z. and Kopelman R., Analytical Properties and Sensor Size Effects of a Micrometer-Sized Optical Fiber Glucose Biosensor, Anal. Chem. 1996, 68, 1408-1413.

\* cited by examiner

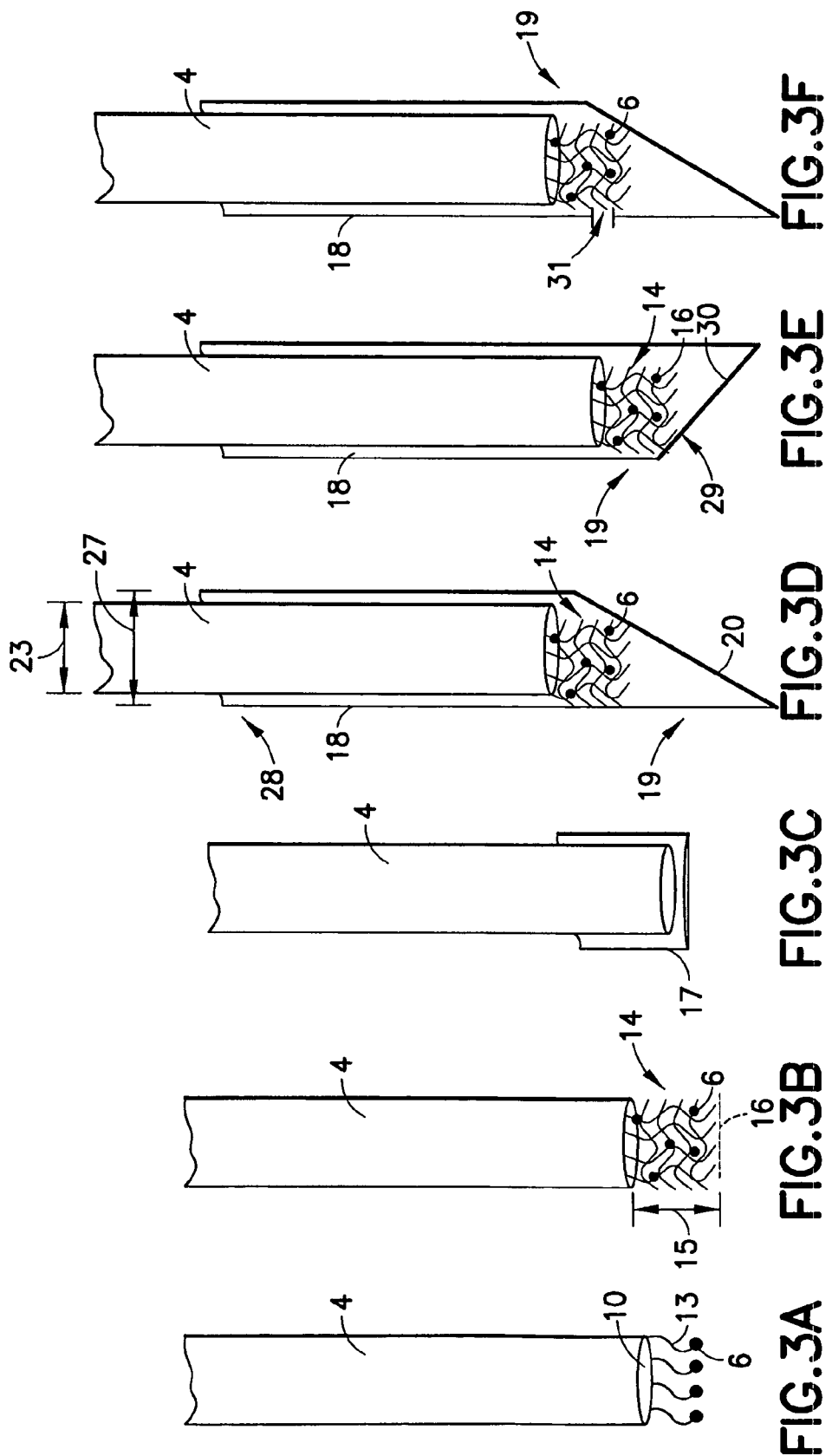

FIBER OPTIC DEVICE FOR SENSING ANALYTES AND METHOD OF MAKING SAME

CROSS-REFERENCE TO RELATED APPLICATIONS

The present application is a continuation-in-part of co-pending U.S. patent application Ser. No. 10/721,797, filed Nov. 26, 2003, the content of which is incorporated by reference in its entirety.

FIELD OF THE INVENTION

The present invention relates to a device that can be used to monitor concentrations of physiologically relevant compounds.

BACKGROUND OF THE INVENTION

Monitoring in vivo concentrations of physiologically relevant compounds to improve diagnosis and treatment of various diseases and disorders is a desirable goal and would enhance the lives of many individuals. Advances in this area show particular promise in the area of facilitating adequate metabolic control in diabetics. Currently, most diabetics use the "finger stick" method to monitor blood glucose level, and patient compliance is problematic due to pain caused by frequent finger sticks. As a consequence, there have been efforts to develop non-invasive or minimally invasive in vivo and more efficient in vitro methods for frequent and/or continuous monitoring of glucose in the blood or other biological fluids.

The approaches to frequent and/or continuous in vivo monitoring tend to fall into two general categories: "non-invasive" and "minimally invasive." Noninvasive monitoring determines analyte levels by directly tracking spectroscopic changes in skin and tissue. Infrared radiation and radio wave impedance spectroscopy are examples of this technology. Progress with these approaches has been slow due to the requirement for frequent calibration, reproducible sample illumination, and variances in spectroscopic backgrounds between individuals. The "minimally invasive" approach avoids direct extraction of blood from the body and relies on the monitoring of signal changes in biological fluids using an intermediate sensing element. Biosensors of this type are devices capable of providing specific quantitative or semi-quantitative analytical information using a biological recognition element that is combined with a transducing (detecting) element.

Most conventional systems for frequent or continuous analyte monitoring involve amperometric biosensors that employ enzymes such as glucose oxidase (GOx) to oxidize glucose to glucuronic acid and hydrogen peroxide, generating an electrochemical signal. These sensors are subject to inaccurate measurement due to oxygen deficiency and buildup of oxidation by-products. An accurate measurement of glucose concentrations requires an excess of oxygen, which is generally not present in human blood or interstitial fluid. Also, the electrochemical reaction itself generates a buildup of oxidation byproducts that may inhibit and degrade both the enzyme and its protective layer.

Biosensors based on optical rather than electrochemical signals have also been developed and may offer significant improvements in stability and calibration. For example, referencing an analyte-dependent optical signal against a second analyte-independent signal can correct for sources of noise and instability in the sensor. However, the potential of optical sensing for in vivo analyte detection has not yet been realized. One reason for this is that many current optical sensing methods rely on enzymatic chemistry such as glucose oxidase. In one common method, an oxygen-sensitive fluorescent dye is used to monitor the consumption of oxygen by the GOx enzymatic reaction. Although this is an optical biosensor, with the fluorescence signal level varying with changing oxygen levels, such a sensor is subject to the same problems as amperometric devices based on this same chemistry: oxygen deficiency and enzyme degradation.

To overcome the challenges associated with enzyme sensing (e.g., GOx), whether electrochemical or optical, non-enzymatic protein-based optical or fluorescent sensing is being explored. Labeled concanavalin A and dextran have been used to create a competitive FRET assay; however, this system requires entrapment of both components, and the dynamic range of the assay is limited. See Ballerstadt, R., Schultz, J. S.; "Competitive-binding assay method based on fluorescence quenching of ligands held in close proximity by a multivalent receptor." Anal. Chem. Acta 345 (1-3): 203-212 (1997). See also, Russell, R. J., Pishko M. V., Gefrides C. C., McShane, M. J., Cote, G. L.; "A fluorescence-based glucose biosensor using concanavalin A and dextran encapsulated in a poly(ethylene glycol) hydrogel" Anal. Chem. 71 (15): 3126-3132 (1999).

Another protein-based sensing chemistry uses the *Esherichia coli* (*E. coli*) periplasmic receptor, glucose-galactose binding protein (GGBP) to generate a fluorescence signal in response to glucose binding. See, for example, Tolosa, L., I. Gryczynski, L. R. Eichhorn, J. D. Dattelbaum, F. N. Castellano, G. Rao, and J. R. Lakowicz; "Glucose sensor for low-cost lifetime-based sensing using a genetically engineered protein" Anal. Biochem. 267: 114-120 (1999); Hellinga, H. W., and J. S. Marvin; "Protein engineering and the development of generic biosensors." Trends Biotechnol. 16: 183-189 (1998); Salins, L. L., R. A. Ware, C. M. Ensor, and S. Daunert, "A novel reagentless sensing system for measuring glucose based on the galactose/glucose-binding protein" Anal Biochem 294: 19-26 (2001); and de Lorimier, R. M., J. J. Smith, M. A. Dwyer, L. L. Looger, K. M. Sali, C. D. Paavola, S. S. Rizk, S. Sadigov, D. W. Conrad, L. Loew, and H. W. Hellinga. "Construction of a fluorescent biosensor family" Protein Sci. 11: 2655-2675 (2002). GGBP undergoes a substantial conformation change upon ligand binding, trapping the ligand between its two globular domains. See, for example, Shilton, B. H., M. M. Flocco, M. Nilsson, and S. L. Mowbray; "Conformational changes of three periplasmic receptors for bacterial chemotaxis and transport: the maltose-, glucose/galactose- and ribosebinding proteins" J. Mol. Biol. 264: 350-363 (1996). By site-specifically labeling the protein with an environmentally sensitive fluorophore this attribute can be exploited to generate a fluorescent signal. See, for example, Salins, L. L., R. A. Ware, C. M. Ensor, and S. Daunert; "A novel reagentless sensing system for measuring glucose based on the galactose/glucose-binding protein" Anal Biochem 294: 19-26 (2001). Because GGBP neither consumes glucose nor generates reaction products, it can be used as a reagentless sensor. This may provide greater accuracy and reliability than amperometric biosensors.

While a number of groups have developed GGBP mutations capable of responding to glucose in the physiological range, there have been no reports of a functional biosensor device based on binding protein technology that is suitable for in vivo or in vitro analyte monitoring. A functional frequent and/or continuous biosensor must couple the sensing element to the optical sensing elements while maintaining sensor integrity and functionality as well as patient comfort. For example, the biological recognition element and accompanying transducing element should preferably be incorporated within biocompatible material that shields the sensing element from the immune system, permits analyte diffusion in and out, and avoids leaching of the sensing element into the patient blood or other biological fluid (e.g., interstitial fluid). Since binding proteins require orientational control and conformational freedom to enable effective use, many physical absorption and random or bulk covalent surface attachment or immobilization strategies as taught in the literature generally are either suboptimal or unsuccessful. Further, a means for interrogating the sample with light in a reproducible and/or controlled fashion must be devised.

One approach generally known is to couple the sensing element to one end of an optical fiber and to couple the optical elements such as excitation sources or detectors to the other end. However, coupling of binding proteins to one end of an optical fiber is subject to the above-mentioned challenge of preserving conformational and/or orientational mobility of the protein. In addition, fiber optic cabling is often impractical from a patient-use point of view since patients may need to remove or replace the sensor periodically. Replacement of the entire fiber can be costly and inconvenient. Finally, the optical system, comprising, e.g., excitation sources, detectors, and other optical elements must be sufficiently robust to tolerate or correct for changes in optical alignment due, for example, to patient motion or drift of the electronics in the optical reader. The optical system must also be sufficiently sensitive to detect signal from reporter dyes without relying on high power consumption and/or large-sized elements that would render the system unportable and hence unwearable.

Accordingly, there is a need for a biosensor that incorporates in its sensing element a binding protein with conformational and/or orientational mobility coupled to optical sensing elements that provide a wearable and robust device.

SUMMARY OF THE INVENTION

The present invention relates to a device for sensing the concentration of a target analyte in a sample. The sample may be blood, saliva, tears, sweat, urine, cerebral spinal fluid, lymph fluid, interstitial fluid, plasma, serum, animal tissue and media. The device generally comprises: (i) an optical conduit having a proximal end and a distal end; and (ii) a sensing element in optical proximity to the distal end of the optical conduit that comprises at least one binding protein that is adapted to bind with at least one target analyte; said sensing element also comprising at least one reporter group.

The optical conduit, which may vary in length from approximately 0.1 cm to 1 meter, couples light into and out of an optical system and into and out of the sensing element. For example, the optical conduit may be a lens, a reflective channel, a needle, or an optical fiber. The optical fiber may be either a single strand of optical fiber (single or multimode) or a bundle of more than one fiber. In one embodiment, the bundle of fibers is bifurcated. The fiber may be non-tapered or tapered so that it can penetrate the skin of a patient.

An optical system may be connected to the proximal end of the optical conduit. The optical system consists of a combination of one or more excitation sources and one or more detectors. It may also consist of filters, dichroic elements, a power supply, and electronics for signal detection and modulation. The optical system may optionally include a microprocessor.

The optical system interrogates the sample either continuously or intermittently by coupling one or more interrogating wavelengths of light into the optical conduit. The one or more interrogating wavelengths then pass through the optical conduit and illuminate the sensing element. A change in analyte concentration results in a change of the wavelength, intensity, lifetime, energy transfer efficiency, and/or polarization of the luminescence of the reporter group, which is a part of the sensing element. The resulting changed luminescence signal passes back through the optical conduit to the optical system where it is detected, interpreted, and stored and/or displayed. In certain embodiments, the optical system comprises multiple excitation sources. One or more of these sources may be modulated to permit dynamic signal processing of the detected signal, thereby enhancing signal-to-noise and detection sensitivity. Modulation may also be used to reduce power consumption by the device or to increase the lifetime of the sensing element by minimizing undesirable phenomena such as photobleaching. The optical system can also include one or more electromagnetic energy detectors that can be used for detecting the luminescence signal from the reporter and optional reference groups as well as for internal referencing and/or calibration. The overall power consumption of the optical system is kept small to permit the device to be operated using battery power.

The sensing element comprises one or more binding proteins that are adapted to bind with at least one target analyte, and at least one reporter group. A suitable binding protein may be any that is adapted for use as a biosensor. For example, the suitable binding protein may be any one of those described in co-pending, commonly owned U.S. Patent Application Publication No. 2003/0153026; U.S. Patent Application Publication No. 2003/0134346; U.S. Patent Application Publication No. 2003/0130167; and U.S. patent application Ser. No. 10/721,091 for "Compositions and Methods for Measuring Analyte Concentrations" to Terry Amiss, et al. filed on Nov. 26, 2003, the contents of which are incorporated herein by reference in their entirety. Suitable binding proteins may also be any one of those described in U.S. Pat. No. 6,277,627, U.S. Pat. No. 6,197,534, or WO 03/060464 A2 the entire contents of which are incorporated herein by reference in their entirety.

The reporter group, which is associated with the binding protein, is adapted to undergo a luminescence change upon binding of the binding protein to the target analyte. As used herein, the term "associated with" means that the reporter group is covalently or non-covalently associated with the binding protein such that upon binding of a target analyte to the binding protein, there is a change in the reporter group's luminescence properties such as wavelength, intensity, lifetime, energy transfer efficiency, and/or polarization. Examples of reporter groups include, but are not limited to, organic dyes, pairs of organic dyes, fluorescent or bioluminescent fusion proteins, pairs of fluorescent or bioluminescent fusion proteins, or any combination of the above. The reporter group may consist of a donor and acceptor undergoing fluorescence resonance energy transfer. Other luminescent labeling moieties include lanthanides such as europium (Eu3+) and terbium (Tb3+), as well as metal-ligand complexes, including those of ruthenium [Ru (II)], rhenium [Re (I)], or osmium [Os (II)], typically in complexes with diimine ligands such as phenanthrolines.

The sensing element is in optical proximity to the optical conduit. "Optical proximity" means that components of the device are close enough to one another such that an optical signal can be transmitted to or received from one object by another. The sensing element may be placed in optical proximity to the optical conduit in a number of ways, for example: attached directly to the optical conduit; attached to a connector that is attached to the optical conduit; attached to a polymer chain or a polymer matrix that is attached to the optical conduit; or attached to a polymer chain or a polymer matrix that is attached to a connector that is attached to the optical conduit. The sensing element may be permanently affixed to the optical conduit or replaceably attached such that the sensing element can be replaced conveniently and economically.

In another embodiment, the sensing element may further comprise one or more reference groups. Unlike the reporter group, the reference group has a luminescence signal that is substantially unchanged upon binding of the target analyte to the binding protein. "Substantially unchanged" means the luminescence change of the reference group is significantly less than the luminescence change undergone by the reporter group. The reference group, which can consist of luminescent dyes and/or proteins, is used for internal referencing and calibration. The reference group can be attached to any number of components of the device including the sensing element, a binding protein not containing the reporter group, the polymer matrix, the polymer chain, a biomolecule that is not a binding protein, the optical conduit, or a tip.

The sensing element (typically this refers to the binding protein with the associated reporter group and optional reference group) may be attached directly to the distal end of the optical conduit using for example covalent, ionic, or van der Waals interactions, dip coating, spin coating, plasma coating, or vacuum deposition. The sensing element may also be attached to a connector, which allows the sensing element to be readily detachable so that it becomes replaceable.

In another embodiment, the sensing element is attached to or immobilized in a polymeric matrix. As used herein, the term "matrix" may be any two dimensional or three-dimensional structure that is permeable to an analyte. The matrix may optionally prevent substantial interference from other biomolecules and may be substantially biocompatible. In one embodiment, the matrix allows the binding protein to retain some degree of conformational and/or orientational mobility. The matrix may consist of multiple layers, with an inner layer serving to retain the binding protein, and one or more outer layers to control the permeability and/or achieve biocompatibility. For example, the polymer matrix may be any one of those described in co-pending, commonly owned U.S. application Ser. No. 10/428,295, filed May 2, 2003. The entire contents of which are incorporated herein by reference. The immobilization may be accomplished either by covalently linking the sensing element to the polymer matrix or by physically entrapping the sensing element within the matrix. In the instance where the polymer matrix physically entraps the sensing element, the matrix pores are sized to retain the sensing element. In the embodiment where the sensing element is attached to the polymeric matrix, the sensing element is attached to the matrix using, for example, covalent or ionic linkage. The polymer matrix can be attached to the distal end of the optical conduit using adhesives, dip or spin coating, plasma coating, covalent, ionic, or van der Waals interactions, a mechanical connector or combinations thereof.

In another embodiment, the sensing element is attached to a polymeric chain. The method of attaching the sensing element to the polymeric chain includes, but is not limited to, covalent, ionic, and van der Waals interactions and combinations thereof. The polymer chain is attached to the distal end of the optical conduit using, for example, dip or spin coating, plasma coating, vacuum deposition, covalent, ionic, or van der Waals interactions, or combinations thereof.

In another embodiment, the device further comprises a tip (either tapered or non-tapered) that is designed to pierce the skin to allow the sensing element to contact body fluids in the intradermal or subcutaneous space. Preferably, the tip is disposable. The tip may be made of plastic, steel, glass, polymer, or any combination of these or similar materials. The tip may be attached directly to the optical conduit (fiber) using adhesives or a mechanical fitting. The tip may also be used to house the optical conduit containing the sensing element, such that it encases the optical conduit and sensing element. In one embodiment, the sensing element may be contained within the tip.

The device may further comprise a connector that may be used to attach the components of the device to one another. The connector may be, for example, any mechanical device, such as standard fiber optic connectors, luer locks, plastic, metal, or glass sleeves, or spring-loaded housings. For instance, the connector may be used to attach the sensing element to the optical conduit, or to attach the optical conduit to the optical system. The primary purpose of the connector is to provide a component that allows the other components to be readily detachable so that the component becomes replaceable.

BRIEF DESCRIPTION OF THE DRAWINGS

The invention will be more readily understood with reference to the embodiments thereof illustrated in the attached drawing figures, in which:

FIG. 3 illustrates various embodiments of the biosensor tip according to an embodiment of the invention;

Throughout the drawing figures, it should be understood that like numerals refer to like features and structures.

DETAILED DESCRIPTION OF THE PREFERRED EMBODIMENTS

Figure 1:
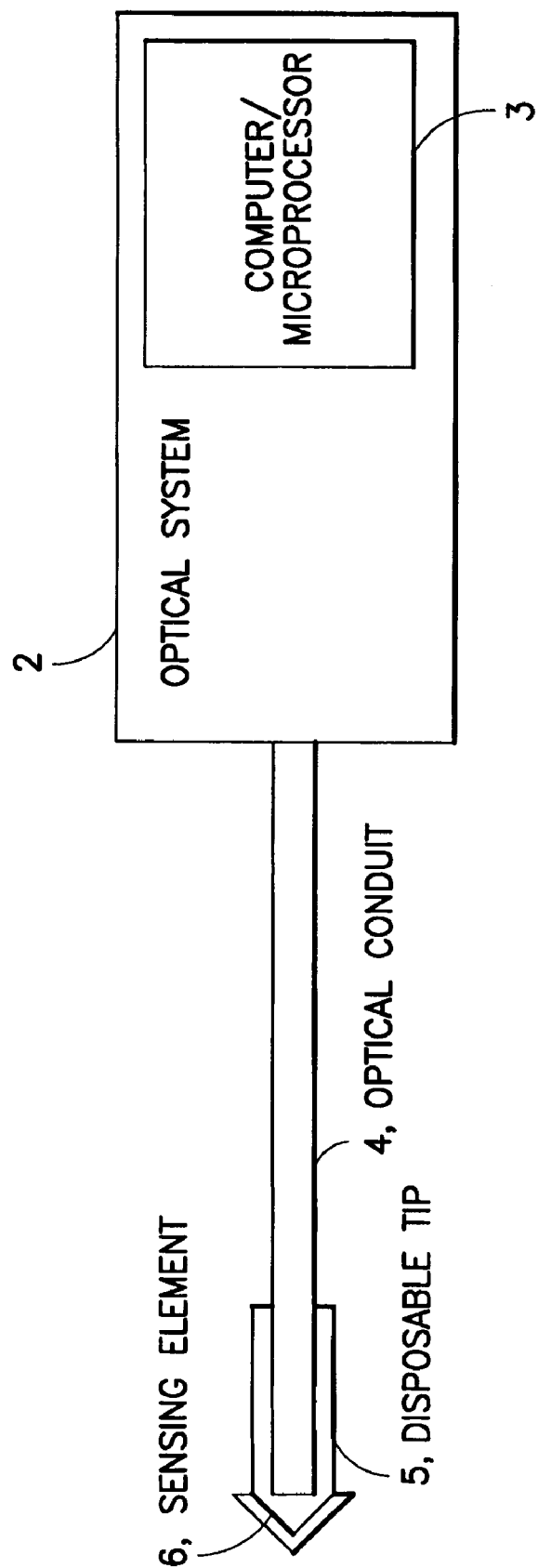
FIG. 1 is a generalized schematic of a biosensor according to an embodiment of the invention.

The preferred embodiments of the invention will now be described with reference to the attached drawing figures. The following detailed description of the invention is not intended to be illustrative of all embodiments. In describing preferred embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

The present invention involves a binding-protein engineered to bind an analyte of interest within a desired clinical or analytical range. In addition, one or more luminescent reporter groups are associated with the binding protein. These luminescent reporter groups include but are not limited to, for example, organic aromatic dye molecules covalently coupled to cysteine residues in the protein or, for example, luminescent biomolecules such as proteins fused to the engineered binding protein. Cysteine or other amino acid groups may be engineered into the binding protein to provide sites of attachment for the luminescent reporter molecule. Binding of the analyte to the binding protein results in a change in the luminescent properties of one or more reporter groups. The luminescent property affected may be the absorption or emission wavelength, absorption or emission intensity, emission lifetime, emission polarization, and/or energy transfer efficiency. Binding of the analyte is also reversible, with the unbinding resulting again in a change in the luminescent properties of the reporter molecule.

The one or more binding proteins along with their associated reporter groups comprise the sensing element. Optionally, the sensing element may also contain one or more reference groups. Unlike the reporter group, the reference group has a luminescence signal that is substantially unchanged upon binding of the target analyte to the binding protein. The luminescence signal from the reference group provides an internal optical standard that can be used to correct for optical artifacts due to for example electronic drift in the optical system or to motion of the sample or optical conduit. The reference group can also be used for calibration. The reference group can be attached to any number of components of the device including the sensing element, a binding protein not containing the reporter group, the polymer matrix, the polymer chain, a biomolecule that is not a binding protein, the optical conduit, or the tip. In one embodiment, the reference group is attached to a binding protein that has been engineered to show no significant response to the analyte at physiologically relevant concentrations.

The sensing element, comprising one or more binding proteins, one or more reporter groups, and optional reference groups, may be immobilized at the end of the optical conduit or inside a disposable tip that interfaces with the optical conduit. Immobilization of the sensing element in the optical conduit or inside the disposable tip may be accomplished by depositing a thin layer of the sensing element, for example, by dip or spin coating, covalent attachment, plasma treatment, and the like directly onto the optical conduit or tip. Alternately, the sensing element can be first immobilized in a polymeric matrix and the matrix then attached to the optical conduit, or tip either by adhesives, injection molding, dip or spin coating, plasma coating, vacuum deposition, ink jet technology, covalent, ionic, or van der Waals interactions, by mechanical attachment or any combination thereof. In an alternate embodiment, a thin layer of sensing chemistry may be attached to the optical conduit and then covered with a semi-permeable membrane.

The optical system is capable of interrogating the luminescent response of the reporter and reference groups by passing light from an electromagnetic excitation source down the optical conduit to the distal end containing the sensing element. The optical system also monitors and interprets the return signals generated by the luminescence response of the reporter group and reference group. The luminescent properties of the reporter group, either wavelength, intensity, lifetime, energy transfer efficiency, or polarization, change in response to analyte binding or unbinding from the binding protein.

Now with reference to FIG. 1, a specific exemplary embodiment of the present invention will be described. The optical system 2 includes a combination of elements including but not limited to electromagnetic energy emitters, electromagnetic energy detectors, various mirrors, filters, electronics, holographic optics, dichroic elements, and optical standards needed to send interrogating radiation from the electromagnetic energy emitter down the optical conduit to the sensing element and then to resolve and interpret the return luminescent signal. The return luminescent signal from the reporter group changes in response to changing concentrations of the analyte to be detected. The optical system 2 may also comprise a computer or microprocessor 3 which handles signal processing, mathematical manipulation of one or more signals, and data storage and handling. The computer or microprocessor 3 may be in physical contact with the other components of the optical system or, in a preferred embodiment, may be physically separated by up to several meters from the other components of the optical system. In this embodiment, information from the electromagnetic energy detectors and electronic processing elements in the optical system is communicated wirelessly to the computer or microprocessor 3. The computer or microprocessor 3 may also store calibration information specific to the sensing element. Light of one or more wavelengths produced in the optical system 2 is channeled down an optical conduit 4 to the sensing element 6. Optical conduit 4 may be either an optical fiber or a short lightguide that transmits light with minimal loss. The sensing element 6 consists of one or more binding proteins with one or more associated luminescent reporter groups either immobilized in a polymeric matrix, attached to a polymer chain, incorporated in a disposable tip, attached directly to the distal end of the optical conduit, or attached to a connector. The sensing element 6 can also consist of additional luminescent reference groups that are optionally attached to biomolecules, polymers, or organic molecules for the purpose of providing a reference or calibration signal. Sensing element 6 can be attached to the distal end of optical conduit 4, either directly or via a polymer matrix, or, in the preferred embodiment, attached to a disposable tip 5 that is attached to the distal end of the optical conduit 4. In this case, the disposable tip 5 is positioned against optical conduit 4 either mechanically, via adhesive, or by any other suitable means known to those of skill in the art.

Figure 2A:
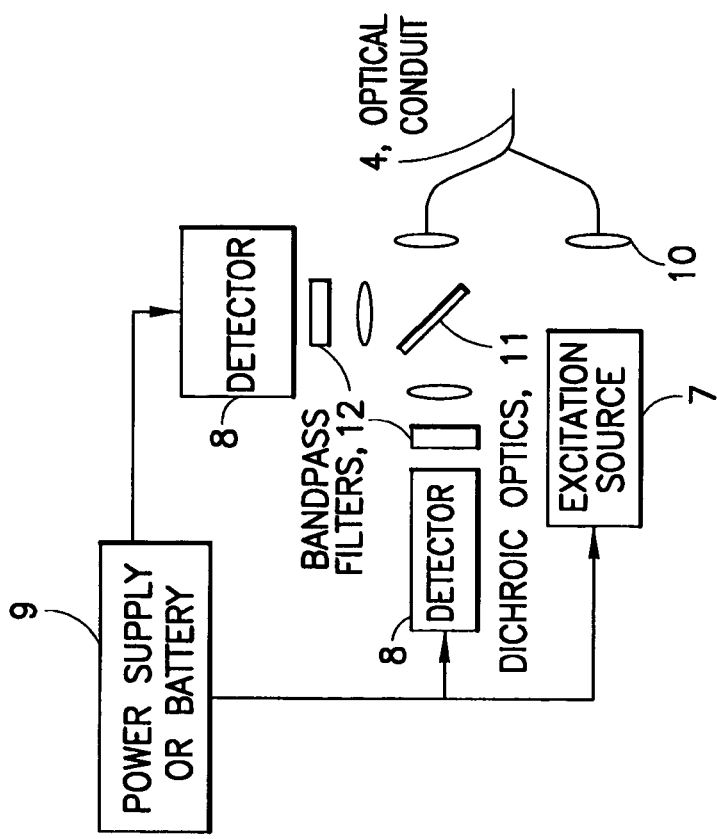
FIG. 2 illustrates two embodiments of the optical configuration in the optical portion of the sensor according to an embodiment of the present invention.

FIG. 2 is an enlargement of the optical system 2 in two typical embodiments. In FIG. 2A, a dichroic mirror or beamsplitter 11 is used to direct light from an electromagnetic energy source 7 to the optical conduit 4. Excitation sources may consist of, but are not limited to, for example arc lamps, laser diodes, or LEDs. In this embodiment, the optical conduit 4 is a fiber optic cable, and the same fiber is used to transmit excitation light from electromagnetic energy source 7 to the sensing element 6 and also to transmit the luminescence signals from the reporter or reference groups back to the optical system 2. A dichroic element II preferably separates the return signal from the excitation light and directs the signal to electromagnetic energy detectors 8. Detectors may consist of, but are not limited to, for example, photodiodes, CCD chips, or photomultiplier tubes. In the event that multiple luminescent signals are returned from the sensing element, additional dichroic elements may be used to direct portions of the return signals to multiple detectors. Preferably, a luminescent reference group that is analyte insensitive is included along with the analyte-dependent reporter molecule to provide a reference signal. This reference signal can be used, for example, to correct for optical or electronic drift.

Figure 2B:
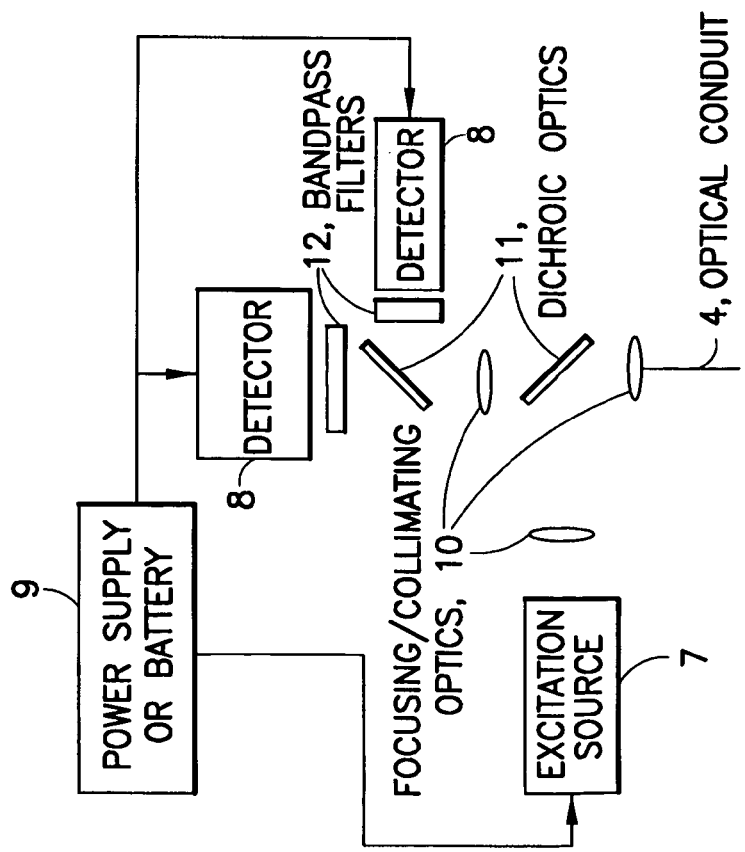

FIG. 2B illustrates a second embodiment in which a bifurcated optical bundle or fused optical fiber arrangement is used to transmit light to and from the sensing element. Here, light from excitation source 7 is transmitted down one arm of the bifurcated fiber bundle. Return luminescent signals from the sensing element are detected using the second arm of the bifurcated fiber, so that in this case the fiber bundling serves to separate excitation from return luminescence. Dichroic optics, beamsplitters, or polarizers may additionally be used to further divide the return luminescence, based for example on wavelength or polarization. Optionally, bandpass filters 12 can be used to select the luminescent wavelength to be detected. Power supply 9 supplies power to the optical system 2.

FIG. 3 illustrates various representative methods or means of attaching the sensing element 6 to the end of an optical conduit 4, when, for example, the optical conduit comprises an optical fiber. One skilled in the art will recognize that in all of the representative attachment methods shown in FIG. 3, attention must be given to design considerations such as obtaining sufficient or intimate contact between the sensing element 6 and the optical fiber 4, preventing delamination of the sensing element 6 from the optical fiber in operation to ensure that light is efficiently transmitted to and from the sensing element 6. Furthermore, maintaining the integrity of the sensing element during operation is important to ensure that a reliable signal response may be obtained. For example, when used in vivo sensing element 6 may be subject to various environments which may cause shrinkage, swelling, deterioration, or negatively impact other desirable functional characteristics including signal intensity, luminescence, response time, etc. Thus, optimal attachment methods or means may vary depending on the characteristics, configuration, and dimensions of the particular sensing element or particular application. Although all of the embodiments shown in FIG. 3 generally depict the distal end 10 of optical fiber 4 as a flat surface at a right angle to the axis of optical fiber 4, in alternate embodiments the distal end 10 may be a complex/compound/curved surface and/or may be tapered or angled with respect to the axis. The attachment methods shown in FIG. 3 are preferred embodiments and may be used either individually or in combination.

In one particular embodiment, the sensing element 6 may be attached directly to the distal end 10 of the optical fiber 4 using for example covalent, ionic, or van der Waals interactions, dip coating, spin coating, plasma coating, vacuum deposition, ink jet technology, or combinations thereof. Referring to FIG. 3A, alternatively the sensing element, comprising the binding proteins, associated reporter groups, and optional reference groups, can be attached to a polymer 13, such as for example a monolayer or long chain polymer, and the polymer 13 attached directly to the distal end 10 of the optical fiber 4 using for example, dip or spin coating, plasma coating, vacuum deposition, covalent, ionic, or van der Waals interactions, ink jet technology, or combinations thereof.

Referring to FIG. 3B, in another embodiment the sensing element 6 may be immobilized in a polymeric matrix 14 and the polymer matrix 14 may be attached to the distal end 10 of the optical fiber 4 using, for example, adhesives, dip or spin coating, plasma coating, injection molding, ink jet technology, covalent, ionic, or van der Waals interactions, a mechanical connector or combinations thereof. In a preferred embodiment, reactive groups of the polymer matrix 14 and protein are used to covalently bond the sensing element 6 directly to the optical fiber 4, such as for example by introducing amine groups on the distal tip or surface 10 of a glass or silica fiber. Matrix 14 is preferably configured and dimensioned to optimize signal transmission or signal magnitude versus response time. In this regard, in a preferred embodiment the height or distance 15 that matrix 14 extends from the distal surface 10 of optical fiber 4 is between about 5 microns or less to about 1 mm. For example, in one exemplary operation the response time was about 3 seconds when matrix height 15 was about 50 microns. Generally, as matrix height 15 is lessened, a shorter response time is achieved, however the signal response time may vary depending on other conditions, such as, for example, the exact dimensions, hydration state, or the particular application. In one alternative embodiment the distalmost surface 16 of matrix 14 may include a reflective or light scattering material layer with the light reflecting surface facing optical fiber 4 to improve luminescence and/or amplify the return signal. In one variation, the reflective material layer may comprise a plasma or sputter coating or a thin film light scattering surface attached to matrix 14. In yet another embodiment, light reflecting particulate matter may be dispersed throughout the matrix to increase the light scattering effect.

Referring to FIG. 3C, in another embodiment a plastic or polymer sleeve 17 may be positioned over the distal end of the optical fiber 4 to house and/or protect the sensing element (not shown). The sensing element may be entrapped in or attached to a polymer matrix as shown in FIG. 3B. The polymer matrix, either containing the sensing element or without, can be introduced into the sleeve either by injection, pouring, or dipping and can then be cross-linked or polymerized within the sleeve 17. If the polymer matrix is introduced into the sleeve without the sensing element, the sensing element may be subsequently introduced or diffused into the polymer matrix to entrap, bind or covalently attach the sensing element to the matrix. Alternatively, the sensing element 6 may be polymerized within the sleeve 17 prior to insertion of the optical fiber 4. In operation, sleeve 17 including sensing element 6 and optical fiber 4 may be implanted in vivo for continual or episodic use. In an alternative embodiment wherein sensing element 6 is positioned within sleeve 17, sleeve 17 may be removably coupleable to optical fiber 4 and optical fiber 4 may be removably insertable into and out of sleeve 17 such that all or part of sleeve 17 may remain in vivo and optical fiber 4 may be inserted and removed as desired for episodic use. In alternate embodiments, different housings may be used in place of sleeve 17.

Referring to FIG. 3D, another embodiment is shown wherein the optical fiber 4 is held within the inside of a needle 18. As used herein, the term "needle" includes but is not limited to micro-needle. The needle 18 may have a modified distal end 19 such as a bevel 20 to control piercing depth and/or one or more side ports to permit access of the analyte to the sensing element 6 contained in needle 18. The sensing element 6 may be positioned inside the needle 18 such that it may be attached directly to optical fiber 4 using any of the methods described in the discussion of FIGS. 3A, 3B, or 3C or, alternatively, may have only mechanical contact with optical fiber 4. In alternate embodiments, the distal end of needle 18 may be crimped to mechanically fix sensing element 6 to needle 18. In a preferred embodiment the external diameter 23 of optical fiber 4 is between about 50-400 microns, preferably between about 50-200 microns and the internal diameter 27 of needle 18 is dimensioned slightly larger than the external diameter 23 to accommodate the insertion of optical fiber 4 into needle 18. In one variation, needle 18 may be mechanically fixed to optical fiber 4 by, for instance, friction fit or crimping needle 18 onto optical fiber 4. In alternate embodiments, optical fiber 4 may be chemically fixated inside needle 18 by glue or any other suitable means known to those skilled in the art. In this regard, a biosensor tip assembly including a needle with an integrated optical fiber and sensing element may be manufactured to be disposable for episodic use or may remain in vivo for continual use. In another embodiment, optical fiber 4 may be removably insertable into and out of needle 18 such that needle 18 may remain in vivo and optical fiber 4 may be inserted and removed as desired for episodic use. In one preferred embodiment, the proximal end 28 of needle 18 includes an optical coupling member configured and dimensioned to receive an attachable optical component thereto for instance to connect or interface to an optical system such as that shown in FIG. 2A or 2B. In a preferred embodiment needle 18 is a straight needle, although in alternate embodiments needle 18 may be have one or more bends or bending portions anywhere along its length. Furthermore, in another alternative embodiment shown in FIG. 3E, the distal end of needle 18 may include a bent tip portion 29 at distal end 19 extending distally beyond and adjacent to matrix 14 and may include a reflective or light scattering surface or layer 30 with the light reflecting surface facing optical fiber 4 to improve luminescence and/or amplify the return signal. Referring to FIG. 3F, another embodiment of a needle assembly is shown wherein the distal end 19 of needle 18 includes one or more ports or holes 31 through which the analyte may flow or migrate to permit access of the analyte to the sensing element 6 contained in needle 18.

Figure 4:
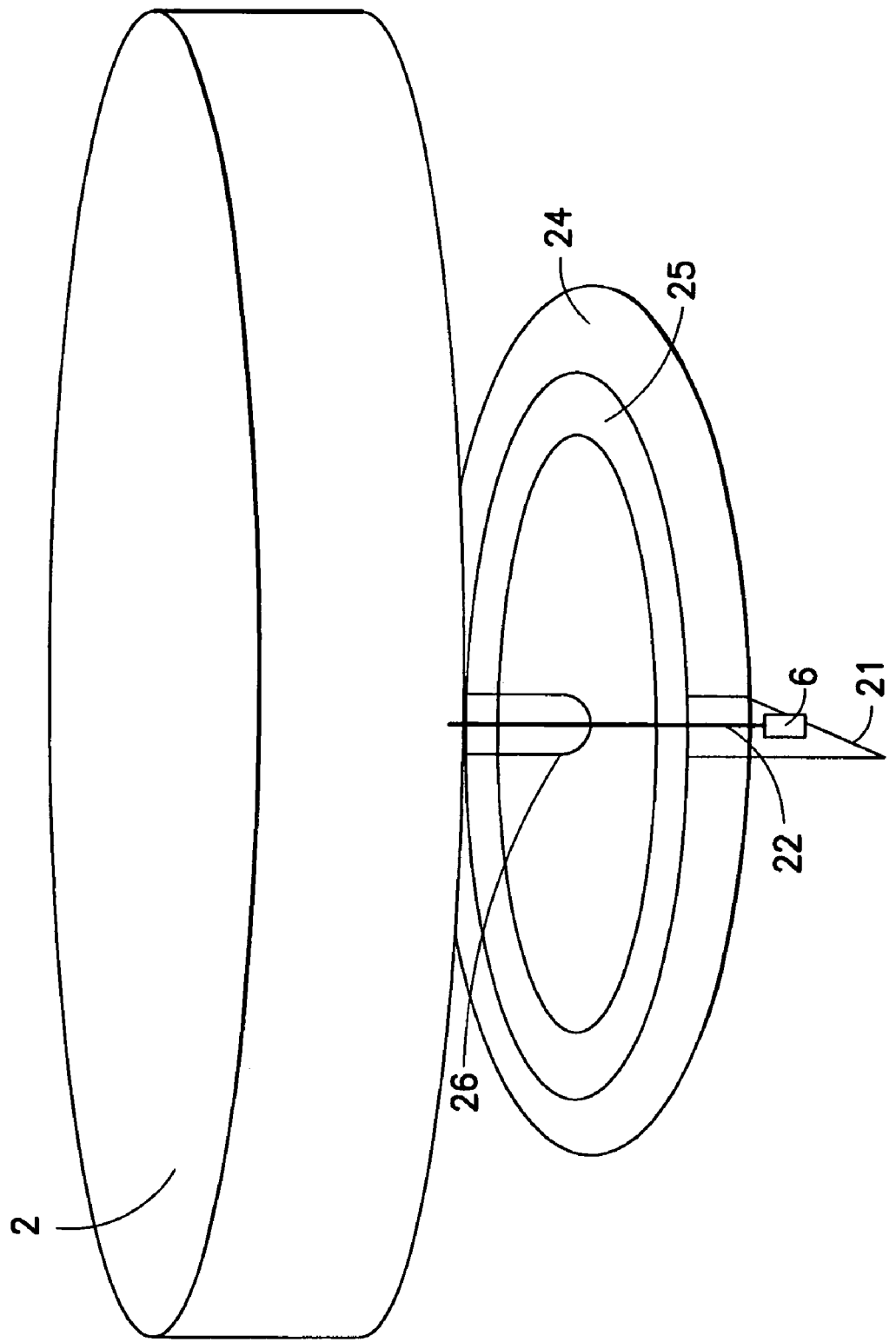
FIG. 4 illustrates an embodiment of the invention that is a wearable in vivo optical biosensor.

FIG. 4 shows an exemplary embodiment of a wearable optical biosensor. In this embodiment, the tip body 21 comprises a steel needle approximately 1-10 mm in length containing within it the sensing element 6 immobilized or fixed onto an optical fiber 22. The fiber 4, sensing element 6, and needle 21 are positioned in a mount 24. The tip body or needle 21, containing the optical fiber 4 and the sensing element 6, is inserted perpendicularly into the skin of a patient so that the sensing element 6 resides in either the intradermal or subcutaneous space. In an exemplary embodiment, needle 21 is fixedly mounted on a mount 24 such that a controlled insertion depth may be obtained. In this regard, needle 21 preferably extends into the skin of a patient a distance between about 0.1 mm to about 10 mm, most preferably between about 1 mm to about 2 mm. Adhesive ring 25 then holds the mount plus needle assembly in place. The optical system 2 then clamps over the mount plus needle assembly, with the connector 26 interfacing the optical fiber 22 with the optical system 2. The optical reader can also be separated from the platform by, for instance, approximately 0.02-1 meter and connected to the rest of the system with an optical fiber. The optical system can be designed, for example, according to either optical embodiment shown in FIG. 2A or 2B. Excitation sources may consist of, but are not limited to, for example arc lamps, laser diodes, or LEDs. Detectors may consist of, but are not limited to, for example, photodiodes, CCD chips, or photomultiplier tubes. In an alternative embodiment, a plurality of tip bodies or needle assemblies 21 may be attached to a single mount 24. In this regard the tip bodies or needle assemblies may be configured to test multiple analytes wherein each needle assembly is configured to test a single analyte. In another embodiment, tip bodies or needle assemblies may be attached to mount 24 such that a drug may be delivered through at least one tip body or needle assembly. Thus, a drug delivery system may be designed such that a proper dosage of drug may be calculated based upon the testing of an analyte and delivered via a tip body or needle assembly attached to the same biosensor mount 24. In this embodiment, the tip body or needle assembly used for drug delivery may comprise one or more ports to deliver the drug therethrough. In yet another embodiment, a temperature probe may be contained within, adjacent to, or attached to at least one tip body or needle assembly. This temperature probe could be, for example, a thermocouple or an optical temperature monitor using, for example, a temperature sensitive fluorophore. In another variation, the biosensor tip can be incorporated into a wearable patch device, wherein the proximal end of the tip body is attached to a patch and the patch is configured and dimensioned to be worn on the exterior skin of the patient. In another embodiment, the biosensor tip may be incorporated into a watch, wherein the proximal end of the tip body is attached to a watch and the watch is configured and dimensioned to be worn on the exterior wrist area of the patient.

In all of the aforementioned embodiments, the assembled fiber and sensing element or manufactured tip device is sterile. In this regard, "sterile" means essentially free of microorganisms or bacteria. In one method of manufacture, the assembled components may be sterilized periodically after each step of manufacture. For example, in the embodiment shown in FIG. 3C, the sleeve may be sterilized after each step of manufacture ultimately ending in an aseptically packaged device. Alternatively, the assembled fiber and sensing element or manufactured tip device can be sterilized in a terminal step.

The following examples illustrate certain preferred embodiments of the instant invention, and are merely intended to be illustrative of exemplary embodiments. Labeled mutated binding proteins with fluorophore reporter probes are used herein in accordance with the procedure set forth by Cass et al., *Anal. Chenz.* 1994, 66, 3840-3847, or as otherwise described.

EXAMPLE 1

According to one embodiment of the present invention, glucose galactose binding protein (GGBP) was used with a triple mutation including a cysteine substituted for an glutamic acid at position 149, an arginine substituted for an alanine at position 213 and a serine substituted for leucine at position 238 (E149C/A213R/L238S). The protein was labeled at the 149 position with N,N'-dimethyl-N-(iodoacetyl)-N'-(7-nitrobenz-2-oxa-1,3-diazol-4-yl)ethylenediamine (IANBD amide)oxy. This mutated GGBP (E149C/A213R/L238S) is specific for glucose, and the reporter group undergoes a fluorescence intensity change in response to glucose binding.

A multicoated or multilayer matrix was prepared as follows. A core matrix was formed by mixing 1 part luminescent or dye-labeled binding protein (15 uM in PBS buffer, pH 7.4, prepared as described in PCT/US03/00203) with 2 to 4 parts 3 wt % alginate (v/v) in a scintillation vial and vortexing at slow speed. 3 mL of the resulting protein-alginate mixture was placed in a syringe and infused at a rate of 10 mL/hr into 200 ml of 1 M $CaCl_2$ on a mixer, thereby forming beads of about 0.4 to 1.5 mm in diameter. The beads were mixed in $CaCl_2$ solution on the mixer for 15-60 minutes. A containment layer was then formed by placing the beads from above in a solution of poly-L-lysine 0.01% w/v in water, approximately 10 mL, for 1 hour, then drying the poly-lysine coated beads on an absorbent towel for 15 to 30 minutes. At this point the sensor was ready to be used.

The fiber used in this embodiment was a bifurcated fiber optic. It contained six 400 um fibers arranged around a central 400 um fiber. The six fibers were used as the excitation conduit and the central fiber as the detection conduit. The total diameter of the fiber was 1.4 mm. Once the fiber was polished, Loctite 401 1medical grade glue was used to adhere the sensing element to the distal end of the fiber optic. The proximal end of the fiber was bifurcated, with one arm going to an excitation source and the other arm going to a detector. A 470 nm LED was used as the excitation source, and a commercial fluorescence spectrometer was used as the electromagnetic energy detector. The emission intensity at 540 nm was then measured.

Figure 5:
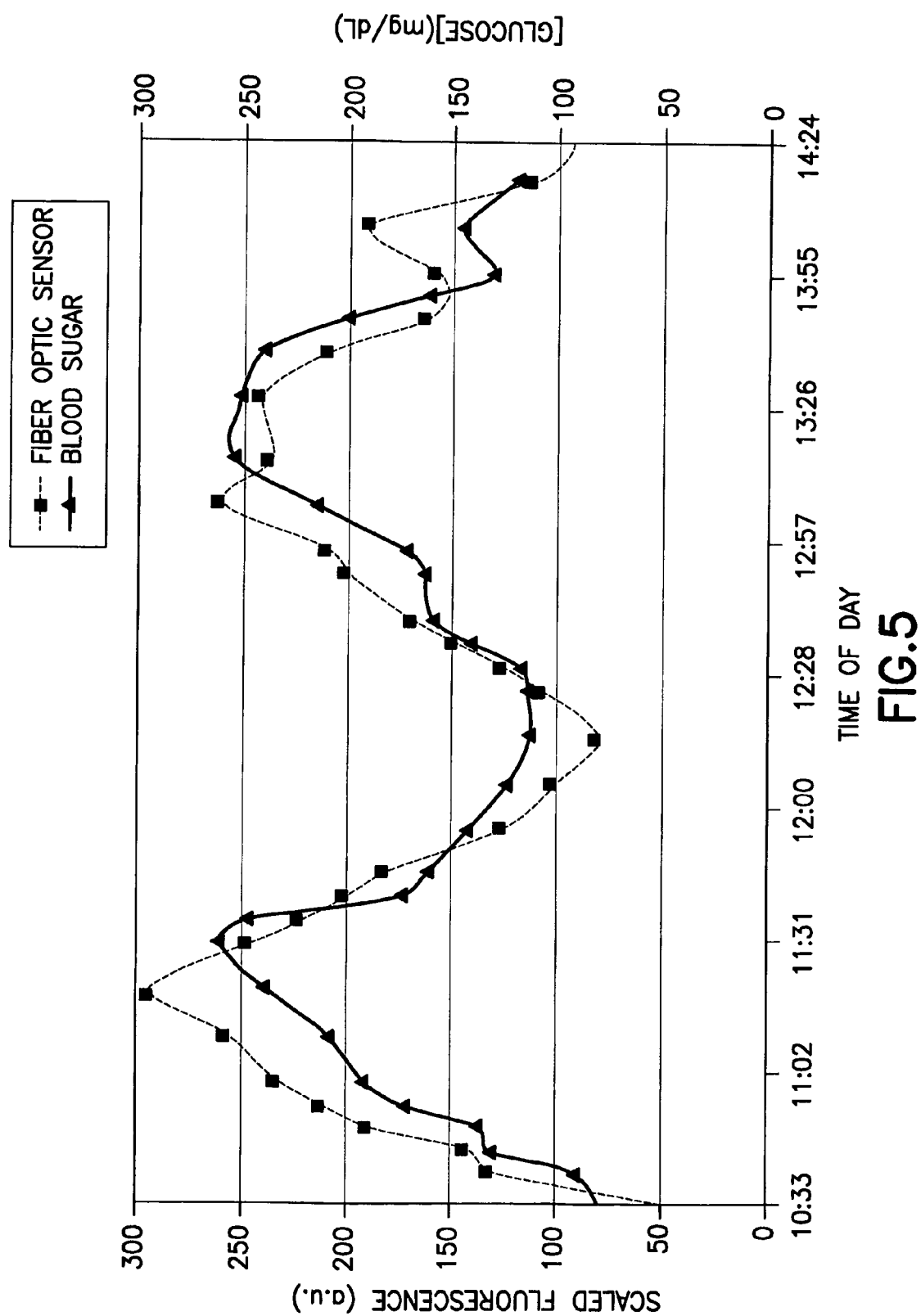
FIG. 5 is a chart showing the performance of a fiber optic biosensor according to an embodiment of the invention tracking changing glucose levels in an anesthetized pig.

In a trial, the distal end and sensing element of a biosensor formed in this manner was inserted through a 13 gauge needle into the side of an anesthetized pig, approximately 1-2 mm under the skin. Alternating solutions of lactated ringer's with and without 10% dextrose were infused through the ear vein of the pig to increase and decrease the pig's glucose levels in a controllable fashion. At intervals, blood samples were pulled from the vena cava of the pig through a throat catheter, and blood sugar readings were tested on a handheld blood glucose meter. The fluorescence intensity of the biosensor was observed to track changing glucose levels in the anesthetized pig, as shown in FIG. 5.

EXAMPLE 2

In another embodiment, the binding protein was glucose galactose binding protein (GGBP), with a cysteine substituted for an glutamic acid at position 149, an arginine substituted for an alanine at position 213 and a serine substituted for leucine at position 238 (E149C/A213R/L238S). The protein was labeled at the 149 position with N,N'-dimethyl-N-(iodoacetyl)-N'-(7-nitrobenz-2-oxa-,3-diazol-4-yl)ethylenediamine (IANBD amide). The biosensor was prepared by inserting the tip of a 400 micron core diameter fiber into a short piece of catheter tubing, and allowing the catheter tubing to overhang the fiber tip by 0.1-1 mm. The fiber comprised a silica core, silica cladding, and polyimide buffer. The fiber diameter was 400/440/470 microns, where the slashes denote diameters measured from the core cladding buffer exteriors.

The immobilization matrix was a crosslinked alginate-based hydrogel, prepared by covalently crosslinking Pronova™ UP LVG alginate through the carboxyls with adipic acid dihydrazide (AAD) via carbodiimide chemistry. Pronova™ UP LVG was selected in this embodiment for its low viscosity and high guluronic to mannuronic ratio. A 2% alginate solution was prepared by dissolving 1 gram of alginate in 50 mL 0.1 M MES buffer (pH 6.5) and then adding 110 mg of AAD and 79 mg of hydroxybenzotriazole (HOBt). The solution was stored at 4° C. until used. To the alginate solution, 145 mg of 1-ethyl-3-(3-dimethylamino-propyl) carbodiimide (EDC) was added per 10 mL of solution, using a dual-syringe mixing technique. The alginate, AAD, HOBt, EDC mixture was aspirated into a 1 mL syringe, and a blunt 30 gauge needle was attached to the syringe. The needle was primed, and then the tip was inserted into the catheter tubing mold on the optical fiber. The catheter tubing on the fiber was filled, ensuring good contact between the tip of the fiber optic and the alginate matrix. The matrix was allowed to cross-link for 15 minutes, and then the fiber tip and matrix assembly were transferred to a 0.1M, 6.5 pH MES solution, where they were stored for 2 hours. At the end of the two hours, the sensing tips were placed in excess phosphate buffer solution (PBS, 0.0027 M potassium chloride, 0.137 sodium chloride, pH 7.4 where they were stored a minimum of 30 minutes to quench the reaction.

To attach binding protein, the tips were incubated in a solution of labeled GGBP in PBS buffer [NBD-E149C/A213R/L238S GGBP] (53 uM, 50 uL) for approximately 8 hours. The sensors were protected from ambient light during incubation. After 8-24 hours of incubation, 50 uL of EDC/NHS (200 mM/50/0 mM) was then added to the incubation tube. After 40 minutes, the sensor tips were removed and placed in 50 uL of 1M, pH 8.5 ethanolamine to quench the reaction. After 20 minutes in the ethanolamine solution, the sensor tips were transferred to PBS solution, where they were allowed to sit for at least 24 hours while unreacted protein diffused out. The sensors were then transferred to fresh PBS and stored in the dark until ready to use.

The fiber in this example was a single, 400 um core multimode fiber (silica core, silica cladding, polyimide buffer). Since in this embodiment the same fiber transmits both the excitation and luminescence signal, dichroic optics were used to separate the luminescence from the excitation, as shown in FIG. 2A. Excitation was with a 470 nm LED. A commercial dichroic filter was used to reflect the 470 nm excitation towards the input end of the fiber and transmit the fluorescence, centered at 550 nm, to the detector. Glass aspheric lenses were used both for beam collimation and to focus light into the fibers and onto the detectors. Scattered excitation was further removed from the detector using a 550 nm bandpass filter. SMA connectors permitted rapid connection and disconnection of the fiber optic sensors. The electromagnetic energy detector of this embodiment was a single photon counting photomultiplier tube. Data acquisition was performed on a laptop computer communicating with the detector through an RS-232 connection.

Figure 6:
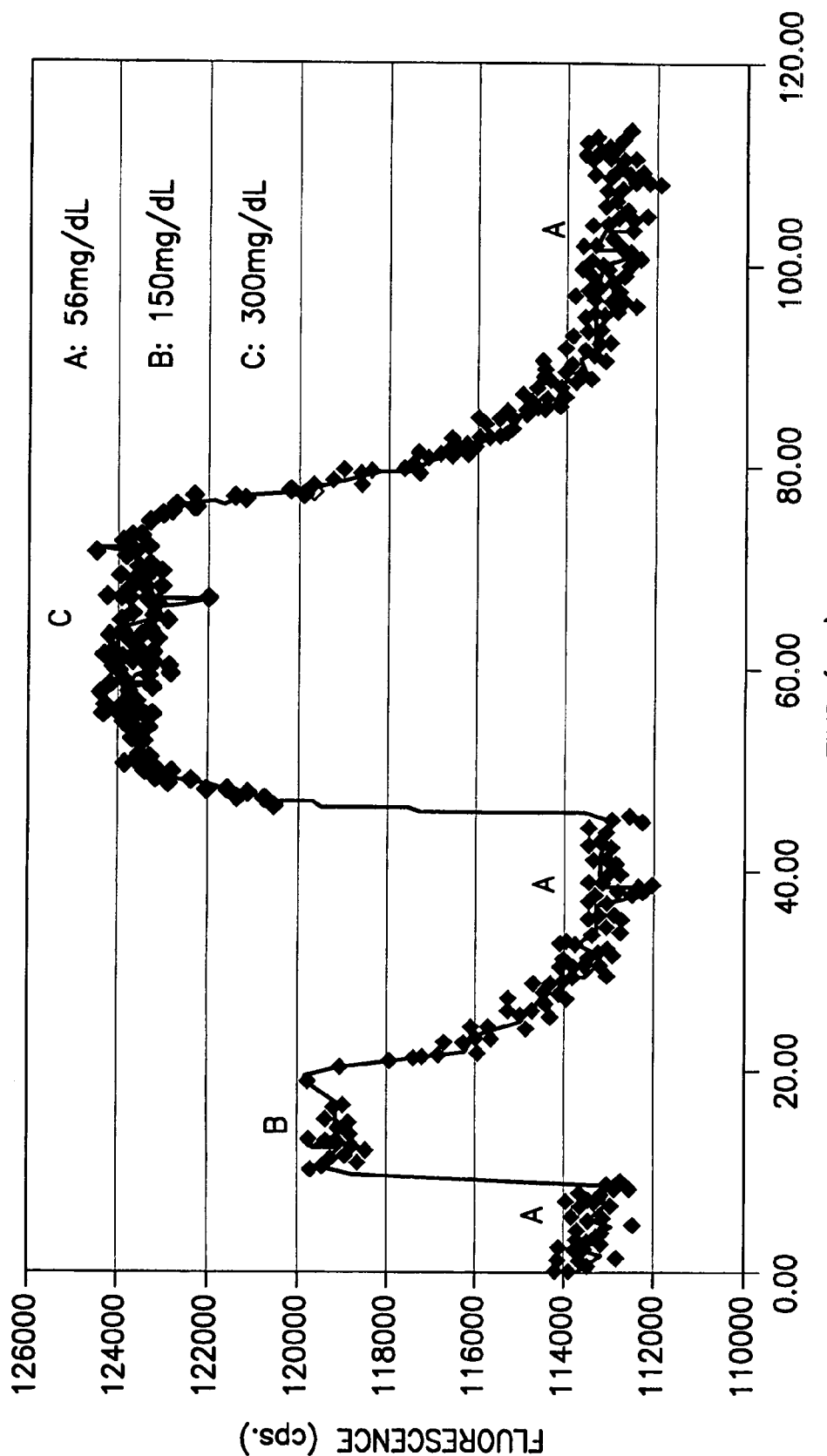
FIG. 6 is a chart showing the performance of a fiber optic biosensor according to an embodiment of the invention using a single 400 micron core fiber optic sensor and the optical configuration illustrated in FIG. 2A.

FIG. 6: In a trial, the distal end and sensing element of a biosensor formed in this manner was inserted into solutions of porcine serum containing different glucose concentrations. All procine serum solutions were filtered through a 200 micron filter, and glucose levels in the solutions were measured on a clinical analyzer. FIG. 6 illustrates the in vitro performance of the sensor. The initial glucose level in the serum was measured to be 56 mg/dL. Serum samples at 150 and 300 mg/dL were prepared by spiking concentrated 1M glucose in PBS into serum aliquots.

EXAMPLE 3

In another embodiment of the present invention, a biosensor was formed by covalent attachment of a thin film to the surface of an optical fiber. The binding protein was glucose galactose binding protein (GGBP), with a cysteine substituted for a glutamic acid at position 149, an arginine substituted for an alanine at position 213 and a serine substituted for leucine at position 238 (E149C/A213R/L238S). The protein was labeled at the 149 position with N,N'-dimethyl-N-(iodoacetyl)-N'-(7-nitrobenz-2-oxa-1,3-diazol-3-yl)ethylenediamine (IANBD amide).

The biosensor was prepared by covalent attachment of an alginate matrix to the amine-functionalized surface of a silica fiber. The fiber comprised a silica core, silica cladding, and polyimide buffer. The fiber diameter was 400/440/470 microns, where the slashes denote diameters measured from the core/cladding/buffer exteriors.

The polyimide buffer was removed from the tip of the optical fiber by exposing the last few millimeters of the fiber to a torch for approximately 1-2 seconds. The residual polyimide was then wiped away. The tip with the buffer removed was then placed in 1 M sulfuric acid for 1 hour. Tips were then rinsed with distilled water, placed in ethanol for 15 minutes, and then submerged in anhydrous toluene for 15 minutes. The cleaned tips were then placed in warm (60° C.) anhydrous toluene containing 1% 3-aminopropyltriethoxysilane (APTES) and allowed to react for 5 minutes. The tips were then removed from the APTES solution and washed with ethanol for 15 minutes. At the end of this process, the presence of amine groups on the surface of the fiber was verified by photoelectron spectroscopy.

An alginate matrix was then applied to the amine-functionalized fiber surface as follows. The immobilization matrix was a crosslinked alginate-based hydrogel, prepared by covalently crosslinking Pronova™ UP LVG alginate, selected for its low viscosity and high guluronic to mannuronic ratio, through the carboxyls with adipic acid dihydrazide (AAD) via carbodiimide chemistry. A 2% alginate solution was prepared by dissolving 1 gram of alginate in 50 mL 0.1M MES buffer (pH 6.5) and then adding 10 mg of AAD and 79 mg of hydroxybenzotriazole (HOBt). A 0.5 mL aliquot of this solution was then mixed with 10 mg of EDC in 50 uL of MES buffer using a dual-syringe mixing technique. The total volume of the solution was approximately 0.55 mL. The alginate, AAD, HOBt, EDC mixture was then transferred to microcentrifuge vials, and the APTES-functionalized fiber tips were submerged in the alginate solution for 3-4 minutes or until the matrix began to solidify. The tips were then removed from the alginate solution, allowed to continue reacting in air for approximately 1-10 minutes, and then transferred to 0.1M, 6.5 pH MES buffer. The tips were allowed to sit in the MES buffer for 2 hours, and then they were quenched in excess phosphate buffer solution (PBS, 0.0027 M potassium chloride, 0.137 sodium chloride, pH 7.7) for a minimum of 30 minutes.

To attach the binding protein, the tips were incubated in a solution of labeled GGBP in PBS buffer [NBD-E149C/A213R/L238S GGBP] (20-60 uM, 50 uL) for several hours. The sensors were protected from ambient light during incubation. After approximately 2-8 hours of incubation, 50 uL of EDC/NHS (200 mM/50 mM) were added to the incubation tube. After 5-40 minutes, the sensor tips were removed and placed in 50 uL of 1M, pH 8.5 ethanolamine to quench the reaction. After 20 minutes in the ethanolamine solution, the sensor tips were transferred to PBS solution, where they were allowed to sit for at least 8 hours while unreacted protein diffused out. The sensors were then transferred to fresh PBS and stored in dark until ready to use.

In a trial of the above described embodiment, the optical reader was the same as described in the previous example, with the exception that the 470 nm excitation was modulated using a solenoid-driven shutter. In addition to interfacing with and controlling the shutters and detectors, the software permitted timed acquisition of fluorescence reading, graphical display of the results, and data analysis and calibration algorithms.

Figure 7:
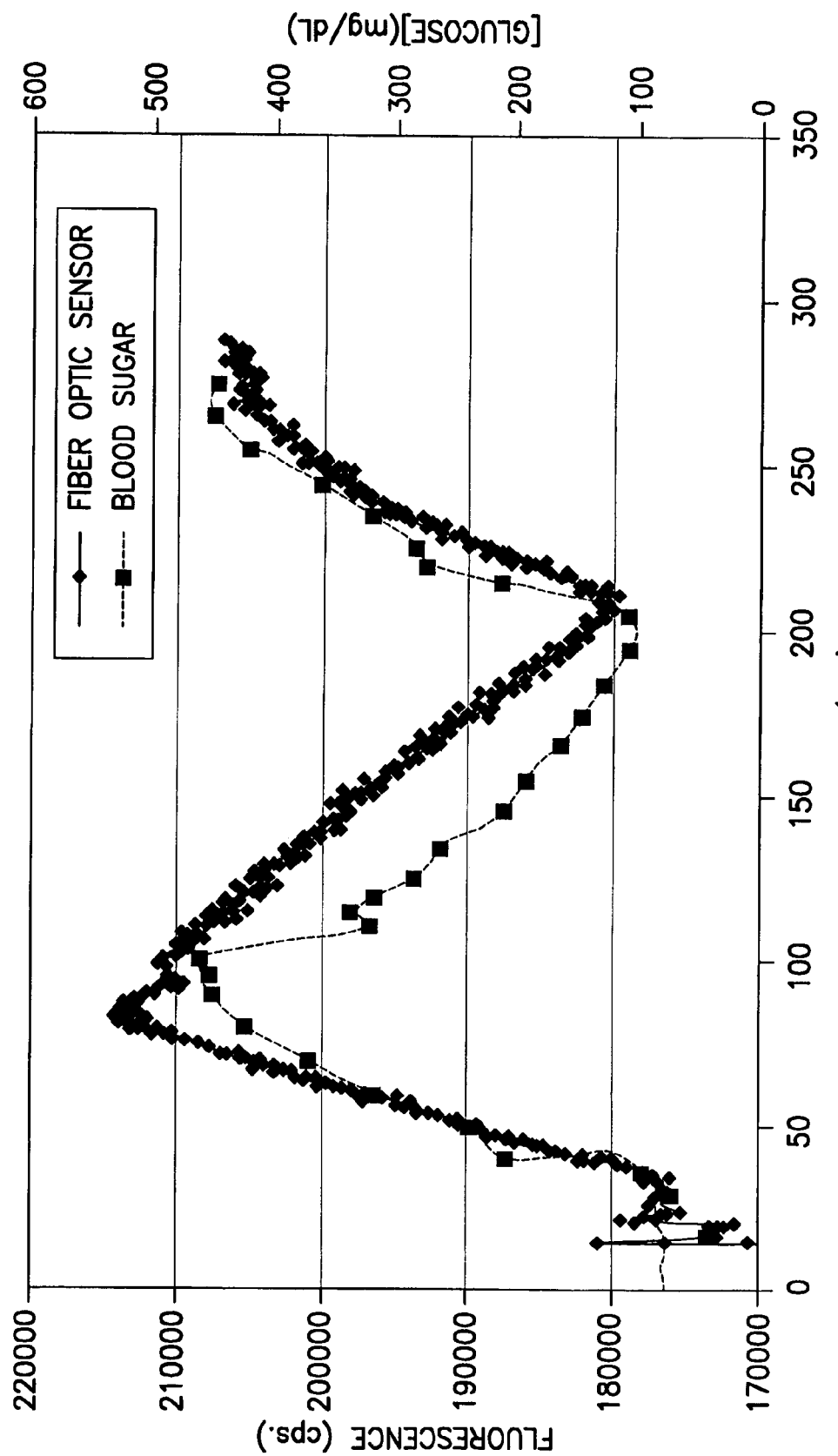
FIG. 7 shows the performance of a fiber optic biosensor according to an embodiment of the invention using a single 400 micron core fiber optic sensor and the optical configuration illustrated in FIG. 2A.

The distal end and sensing element of a biosensor formed in this manner was then inserted in the side of an anesthetized pig. Insertion was done by inserting the fiber either intradermally or subcutaneously through a hole in the skin formed by a 18-24 gauge needle. Alternating solutions of lactated ringer's with and without 10% dextrose were infused through the ear vein of the pig to increase and decrease the pig's glucose levels in a controllable fashion. At intervals, blood samples were pulled from the vena cava of the pig through a throat catheter, and blood sugar readings were tested on a handheld glucose meter. The fluorescence intensity of the biosensor was observed to track changing blood glucose levels in the anesthetized pig, as shown in FIG. 7.

EXAMPLE 4

In another embodiment of the invention, dual wavelength detection with an internal optical reference group was performed. The binding protein was glucose galactose binding protein (GGBP), with cysteine substituted for a glutamic acid at position 149, an arginine substituted for an alanine at position 213 and a serine substituted for leucine at position 238 (E149C/A213R/L238S). The protein was labeled at the 149 position with the reporter group N,N'-dimethyl-N-(iodoacetyl)-N'-(7-nitrobenz-2-oxa-1,3-diazol-4-yl)ethylenediamine (IANBD amide). The reference group was Texas Red® C2 maleimide attached to GGBP with a cysteine substituted for a glutamic acid at position 149 (TR-E149C GGBP). Over the physiological range of glucose concentrations, the luminescence from TR-E149C GGBP is substantially unchanged, and thus TR-E149C GGBP serves as an internal reference for the signal from the analyte-dependent binding protein and reporter group (NBD-E149C/A213R/L238S GGBP].

The biosensor was prepared by inserting the tip of a 400 micron core diameter fiber into a short piece of catheter tubing, allowing the catheter tubing to overhang the fiber tip by 0.1-0.5 mm. The fiber comprised a silica core, silica cladding, and polyimide buffer. The fiber diameter was 400/440/470 microns, where the slashes denote diameters measured from the core/cladding/buffer exteriors.

The immobilization matrix was a crosslinked alginate-based hydrogel, prepared by covalently crosslinking Pronova™ UP LVG alginate, selected for its low viscosity and high guluronic to mannuronic ratio, through the carboxyls with adipic acid dihydrazide (AAD) via carbodiimide chemistry. A 2% alginate solution was prepared by dissolving 1 gram of alginate in 50 mL 0.1M MES buffer (pH 6.5) and then adding 110 mg of AAD and 79 mg of hydroxybenzotriazole (HOBt). The solution was stored at 4° C. until used. Using a dual-syringe mixing technique, a 0.5 mL aliquot of the alginate solution was then mixed with a 50 uL MES solution containing 10 mg of 1-ethyl-3-(3-dimethylaminopropyl) carbodiimide (EDC) and 90 µL of 60 µM TR-E149C GGBP, The alginate, AAD, HOBt, EDC, TR-E149C mixture was aspirated into a 1 mL syringe, and a blunt 30 gauge needle was attached to the syringe. The needle was primed, and then the tip was inserted into the catheter tubing mold on the optical fiber. The catheter tubing on the fiber was filled, ensuring good contact between the tip of the fiber optic and the alginate matrix. The matrix was allowed to cross-link for 15 minutes, and then the fiber tip and matrix assembly were transferred to a 0.1M, 6.5 pH MES solution, where they were stored for 2 hours. At the end of the two hours, the sensing tips were placed in excess phosphate buffer solution (PBS, 0.0027 M potassium chloride, 0.137 sodium chloride, pH=7.4) where they were stored a minimum of 30 minutes to quench the reaction.

To attach binding protein, the tips were incubated in a solution containing IANBD labeled GGBP in PBS buffer [NBD-E149C/A213R/238S GGBP]. The solution of NBD-E149C/A213R/L238S GGBP and TR-E149C GGBP was 60 uM concentration in both species. During the incubation period, the sensors were protected from ambient light. After approximately 2-8 hour of incubation, 50 uL of EDC/NHS (200 mM/50 mM) were added to the incubation tube. After 5-40 minutes, the sensor tips were removed and placed in 50 uL of 1M, pH 8.5 ethanolamine to quench the reaction. After 20 minutes in the ethanolamine solution, the sensor tips were transferred to PBS solution, where they were allowed to sit for at least 8 hours while unreacted protein diffused out. The sensors were then transferred to fresh PBS and stored in the dark until ready to use.

In a trial of the above described embodiment, the fluorescence signal was read using an optical system following the configuration illustrated in FIG. 2A. A 470 nm LED (LS-450) was used for excitation, and two single photon counting photomultiplier tubes were used as electromagnetic energy detectors. A commercial dichroic beamsplitter was used to reflect the 470 nm light from the electromagnetic energy emitter towards the fiber and to transmit the luminescence signals from the reporter and reference groups towards the detectors. A second dichroic beamsplitter was used to separate the luminescence signals from the reporter and reference groups, directing the emission from NBD-E149C/A213R/L238S towards one detector and the emission from TR-E149C GGBP towards the other detector. A 550 nm bandpass filter in front of one detector and a 610 nm bandpass filter in front of the other detector were used to achieve further spectral resolution for NBD-E149C/A213R/L238S and TR-E149C GGBP, respectively.

Figure 8:
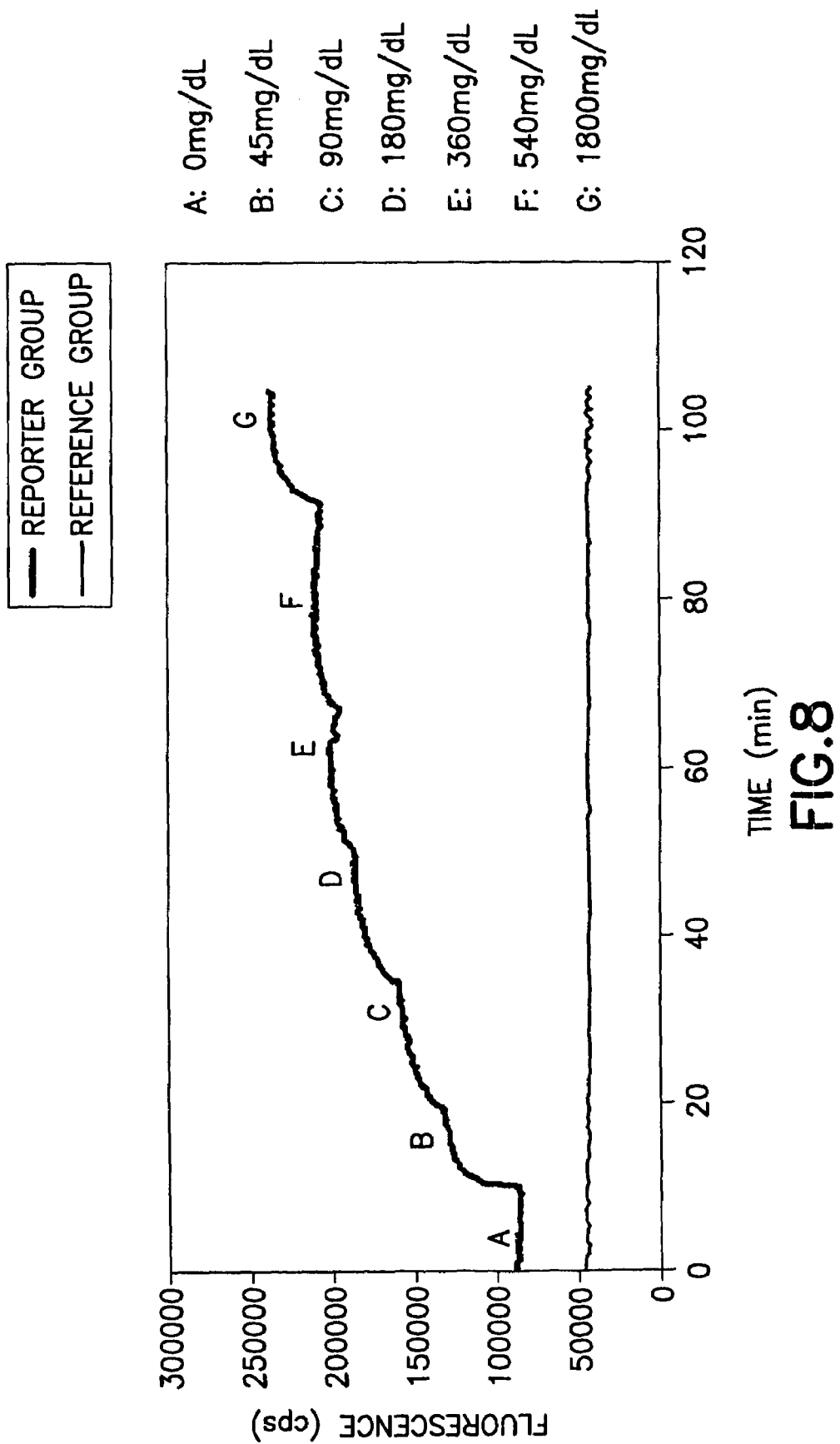
FIG. 8 illustrates an embodiment of the present invention including a multiple detector and an internal reference.

In a trial, the distal end and sensing element of a biosensor formed in this manner was inserted into solutions of PBS buffer containing different levels of glucose. Glucose levels in the solutions were measured on a clinical analyzer. FIG. 8 shows the sensor response to changing glucose levels. The 550 nm signal from the IANBD reporter group tracks changing glucose levels. The 610 nm emission from the Texas Red® reporter group is substantially unchanged as glucose levels vary. However, in this embodiment, a portion of the reporter group's emission also occurs at 610 nm. The detector in the optical system that tracks the 610 nm luminescence signal detects both the emission of the reference group and also the portion of the reporter group (IANBD) emission that occurs in this wavelength region. Since the contribution to the 610 nm signal from the reporter group is a constant fraction of the 550 nm signal, this contribution can be mathematically subtracted from the 610 nm signal to generate the signal due to the reference group alone. When this mathematical manipulation is performed, the 610 nm signal is substantially unchanging with glucose concentration as shown in FIG. 8.

EXAMPLE 5

In another embodiment of the present invention, a biosensor was formed by covalent attachment of a thin film to the surface of an optical fiber. One end of the optical fiber was coupled to a fluorescence detection device, while the other end contained an approximately 50 micron film of an alginate matrix covalently bonded to the surface of the optical fiber.

Coupling of the alginate matrix to the optical fiber was accomplished by first coating the fiber with APTMS via a plasma treatment process. The fiber optic was placed in the midplane of a 12-inch diameter by 18-inch tall upright cylindrical vacuum chamber. An open 1-inch diameter by 2-inch tall vial containing about 5 cubic centimeters of APTMS was placed on an electrode in the chamber. The system was initially evacuated by a turbomolecular pump, backed with a rotary vane roughing pump, to a pressure of about 8 milliTorr. The valve in the pumping line was then throttled back to allow the pressure of the vaporizing monomer to rise to a constant 85 milliTorr. The electrode was then excited by a 13.56 MHz radio frequency power generator, in series with a matching network to deliver 22 watts of power. The plasma so produced was operated for 60 seconds to polymerize the monomer vapor into a film on the fiber surface.

An alginate-based hydrogel matrix was then coupled to the APTMS coating. The alginate hydrogel matrix was prepared by covalently cross-linking Pronova™ UP LVG alginate through the carboxyls with adipic acid dihydrazide (AAD), via carbodiimide chemistry. Pronova™ UP LVG was selected its low viscosity and high guluronic to mannuronic ratio. A 2% alginate solution was prepared by dissolving I gram of alginate into 50 mL 0.1 M MES buffer (pH 6.0) and adding 110 mg of AAD and 79 mg of hydroxybenzotriazole (HOBt). The solution can be stored at 4° C. until needed. To the alginate solution, 196 mg of 1-ethyl-3-(3-dimethylaminopropyl) carbodiimide (EDC) was added per 10 mL of solution, using a dual-syringe mixing technique. The alginate/AAD/HOBt,/EDC mixture was then dispensed into a vial, and the APTMS treated tips of the fiber optic sensor were dipped into the alginate mixture to form an approximately 50 micron thick coating. The alginate matrix was then allowed to cross-link for approximately 2 hrs in a hydration chamber. The sensing tips were then placed in excess pH 8.5 ethanolamine for 15 minutes to quench the reaction and stored in excess 0.1M MES PH 6.5.

To attach the binding protein, the tips were incubated in a solution of labeled glucose-galactose binding protein (GGBP) in 0.1M MES PH 6.5 buffer (100 uM, 50 uL) for approximately 2 hours. The GGBP used in this biosensor was a mutant GGBP, wherein a cysteine was substituted for an glutamic acid at position 149, an arginine was substituted for an alanine at position 213 and a serine was substituted for leucine at position 238 (E149C/A213R/L238S). The mutant GGBP protein was labeled at the 149 position with N-((2-iodoacetoxy)ethyl)-N-methyl)amino-7-nitrobenzoxadiazole (IANBD), as referred to in U.S. Patent Application Publication No. 20030134346A1, the entire contents of which are incorporated by reference. It should be noted, however, that other labeled proteins may be used. The sensors were shielded from ambient light during incubation. After 2 hours of incubation, 50 uL of a solution of 1-ethyl-3-(3-dimethylaminopropyl)carbodiimide 20 mM (EDC)/N-hydroxysulfosuccinimide5 mM/50 mM (sulfo-NHS—Sigma/Fluka) was then added to the incubation tube. After 4 hours, the sensor tips were removed and placed in 50 uL of 1M pH 8.5 ethanolamine to quench the reaction. After 20 minutes in the ethanolamine solution, the sensor tips were transferred to excess PBS solution, where they were allowed to sit for at least 8 hours while any unreacted protein diffused out. The sensors were then transferred to fresh PBS and stored in the dark until ready to use.

Figure 9:
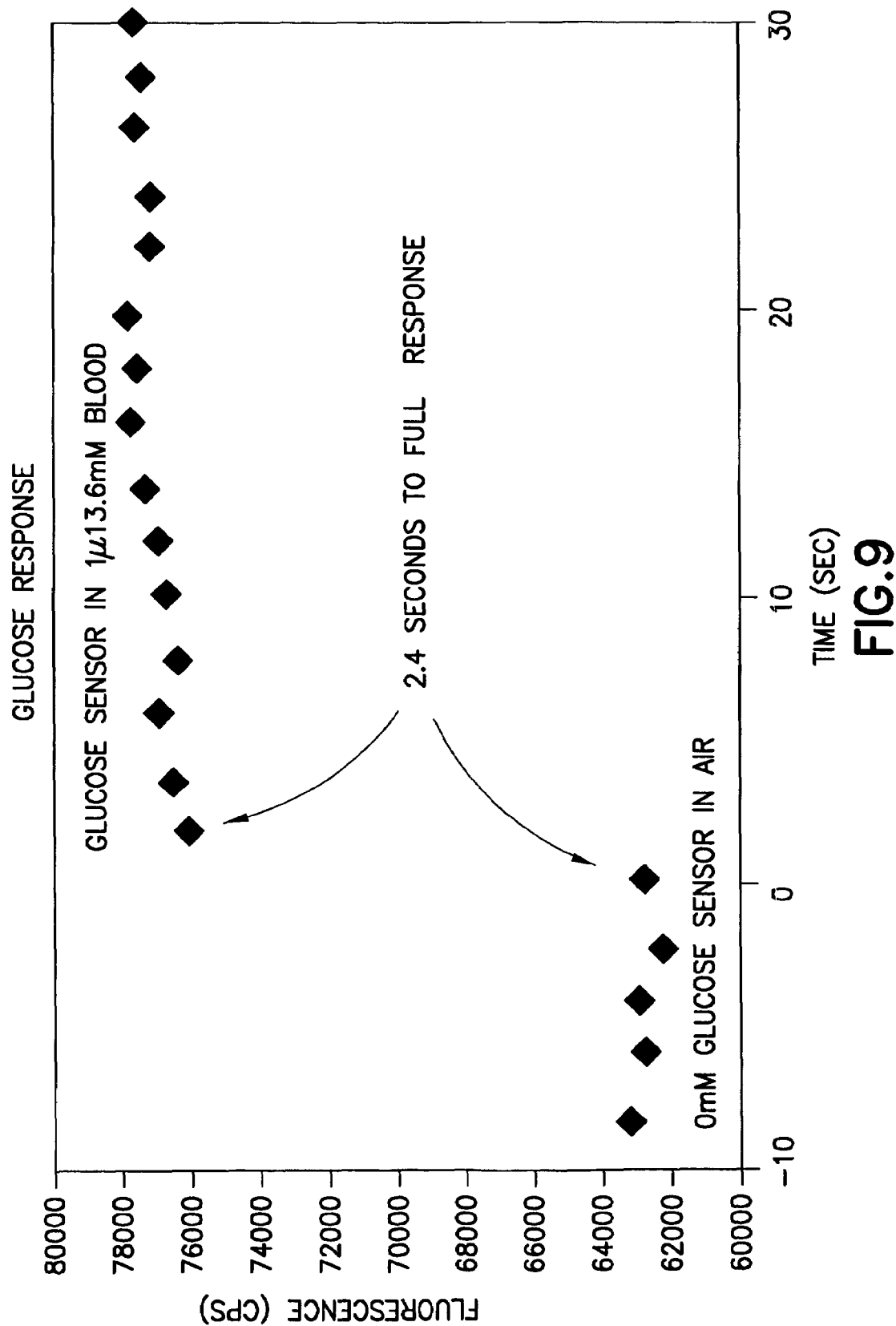
FIG. 9 is a chart showing the performance of an embodiment of a biosensor constructed in accordance with Example 5.

FIG. 9 shows the response of the glucose biosensor to changes in glucose concentrations in swine blood. The sensing end of the fiber was dried to remove excess water outside the protein containing matrix, and then the dried fiber optic sensor was dipped into a 1 microliter sample of pig blood containing 3.6 mg/dL glucose. The fluorescence of the sensor increased in response to the glucose levels in the blood sample, reaching its full fluorescence response in approximately 2.4 seconds.

EXAMPLE 6

Figure 10:
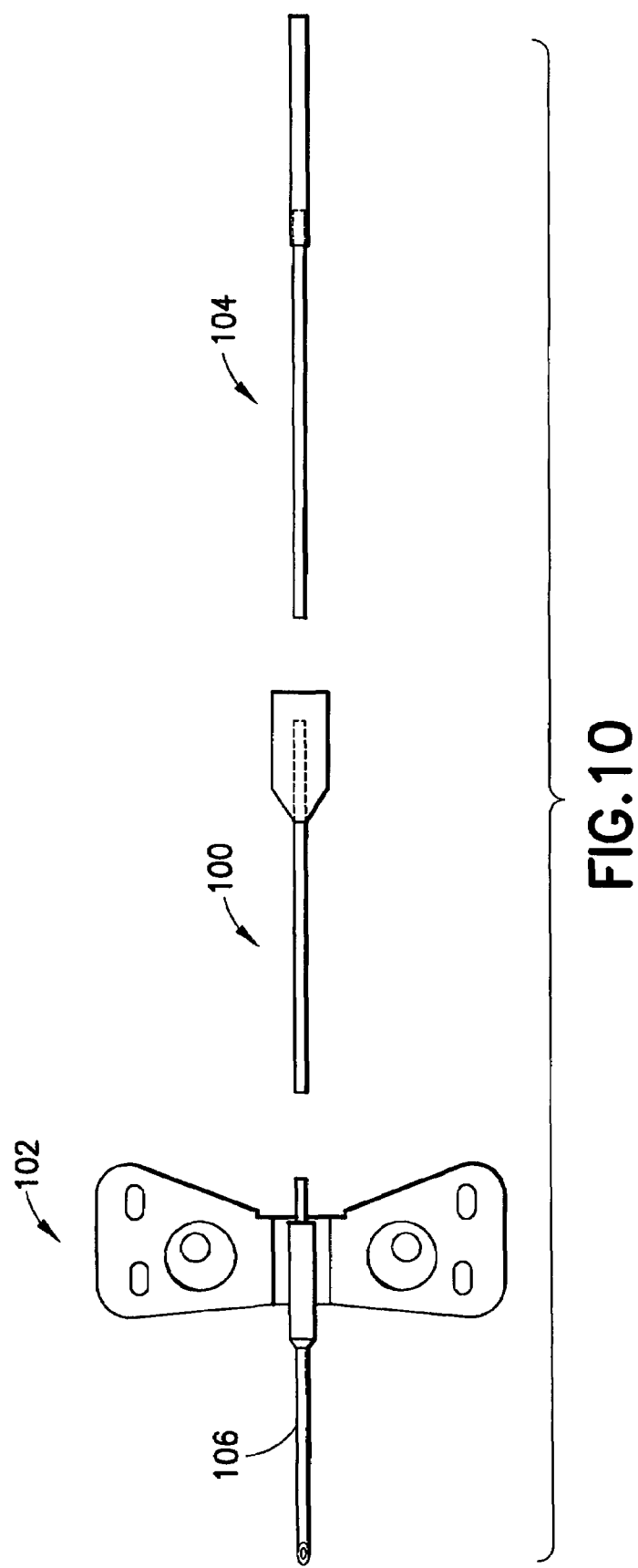
FIG. 10 is an exploded view of an embodiment of a biosensor constructed in accordance with Example 6.

In an example of another embodiment, shown in FIG. 10, a stainless steel tube 100 was used to mate a biosensor tip 102 to an optical conduit 104. The biosensor tip 102 consisted of a small piece of optical fiber (approximately 3 cm), mounted inside a stainless steel needle 106. One end (the "sensing end") of the optical fiber was coated with glucose sensing chemistry, and the other end was polished to provide good optical transmission. The sensing end of the optical fiber was fully contained within the needle and extended approximately 200-400 microns past the heel of the needle bevel at the distal end of the biosensor tip 102.

The fiber used in this example comprised a silica core, silica cladding, and polyimide buffer. The fiber diameter was 400/440/470 +/−~3 microns, where the slashes denote diameters measured from the core/cladding/buffer exteriors. The sensing end of the fiber was amine-functionalized using plasma deposition of APTMS, as described in Example 5 above. Alginate matrix and binding protein were also applied as described in Example 5 with one exception the alginate matrix was applied during cross-linking to the bevel of the needle using one of the mixing syringes with a small blunt needle attached. The binding protein used in this biosensor was a mutant glucose-galactose binding protein (GGBP), wherein a cysteine was substituted for an glutamic acid at position 149, an arginine was substituted for an alanine at position 213 and a serine was substituted for leucine at position 238 (E149C/A213R/L238S). The mutant GGBP protein was labeled at the 149 position with N-((2-iodoacetoxy) ethyl)-N-methyl)amino-7-nitrobenzoxadiazole (IANBD).

The proximal end of the biosensor tip 102 was then reproducibly detached and re-attached from/to the optical conduit 104 leading to the optical instrumentation using a stainless steel connector tube 100. Referring to FIG. 10, in the example given, the connector tube 100 was sized so that the inner diameter of the tube was approximately 20-26 micrometers greater than the outer diameter of the fiber optic/needle and optical conduit assemblies (Optimally this could be smaller, i.e. about 1-12 micrometer size difference). The proximal end of the biosensor tip 102 and the distal end of the optical conduit 104 are polished flat and mate under pressure inside the stainless steel connector tube 100 to facilitate optical transmission from the sensor to the optical instrumentation. The biosensor tip 102 could then be treated as a disposable by releasing it from the stainless steel connector and the optical conduit 104.

EXAMPLE 7

In another embodiment of the present invention, a biosensor was formed by covalent attachment of an alginate matrix to the surface of an optical fiber contained inside a 21 gauge needle. The optical fiber used comprised a silica core, silica cladding, and polyimide buffer. The fiber diameter was 400/440/470 microns, where the slashes denote diameters measured from the core/cladding/buffer exteriors. The proximal end of the optical fiber was polished and mounted into a standard SMA fiber optic connector for attachment to an optical fluorescence instrument. The distal end of the fiber was then inserted into a 21 gauge stainless steel needle, with the tip of the fiber extending approximately 200-500 microns past the heel of the needle bevel.

The fiber optic, needle assembly was then placed in a vacuum chamber for plasma treatment. The fiber optic was placed in the midplane of a 12-inch diameter by 18-inch tall upright cylindrical vacuum chamber. An open 1-inch diameter by 2-inch tall vial containing about 5 cubic centimeters of APTMS was placed on an electrode in the chamber. The system was initially evacuated by a turbomolecular pump, backed with a rotary vane roughing pump, to a pressure of about 8 milliTorr. The valve in the pumping line was then throttled back to allow the pressure of the vaporizing monomer to rise to a constant 85 milliTorr. The electrode was then excited by a 13.56 MHz radio frequency power generator, in series with a matching network to deliver 22 watts of power. The plasma so produced was operated for 60 seconds to polymerize the monomer vapor into a film on the fiber surface.

An alginate-based hydrogel matrix was then coupled to the APTMS coating. The alginate hydrogel matrix was prepared by covalently cross-linking Pronova™ UP LVG alginate through the carboxyls with adipic acid dihydrazide (AAD), via carbodiimide chemistry. Pronova™ UP LVG was selected its low viscosity and high gulronic to mannuronic ratio. A 2% alginate solution was prepared by dissolving 1 gram of alginate into 50 mL 0.1M MES buffer (pH 6.0) and adding 110 mg of AAD and 79 mg of hydroxybenzotriazole (HOBt). The solution can be stored at 4° C. until needed. To the alginate solution, 145 mg of 1-ethyl-3-(3-dimethylaminopropyl) carbodiimide (EDC) was added per 10 mL of solution, using a dual-syringe mixing technique. The alginate, AAD, HOBt, EDC mixture was aspirated into a 1 mL syringe, and a blunt 30 gauge needle was attached to the syringe. The needle was primed, and then the tip was inserted into the bevel of the needle containing the optical fiber. The bevel of the needle was filled, ensuring good contact between the tip of the fiber optic and the alginate matrix. The matrix was allowed to cross-link for 15 minutes, and then the tip and matrix assembly were transferred to a 0.1M, 6.5 pH MES solution, where they were stored for 2 hours. At the end of the two hours, the sensing tips were placed in excess phosphate buffer solution (PBS, 0.0027 M potassium chloride, 0.137 sodium chloride, pH 7.4 where they were stored a minimum of 30 minutes to quench the reaction.

To attach binding protein, the tips were incubated in a solution of labeled GGBP in PBS buffer [NBD-E149C/A213R/L238S GGBP] (53 uM, 50 uL) for approximately 8 hours. The sensors were protected from ambient light during incubation. After 8-24 hours of incubation, 50 uL of EDC/NHS (200 mM/50/0 mM) was then added to the incubation tube. After 40 minutes, the sensor tips were removed and placed in 50 uL of 1M, pH 8.5 ethanolamine to quench the reaction. After 20 minutes in the ethanolamine solution, the sensor tips were transferred to PBS solution, where they were allowed to sit for at least 24 hours while unreacted protein diffused out. The sensors were then transferred to fresh PBS and stored in the dark until ready to use.

Figure 11:
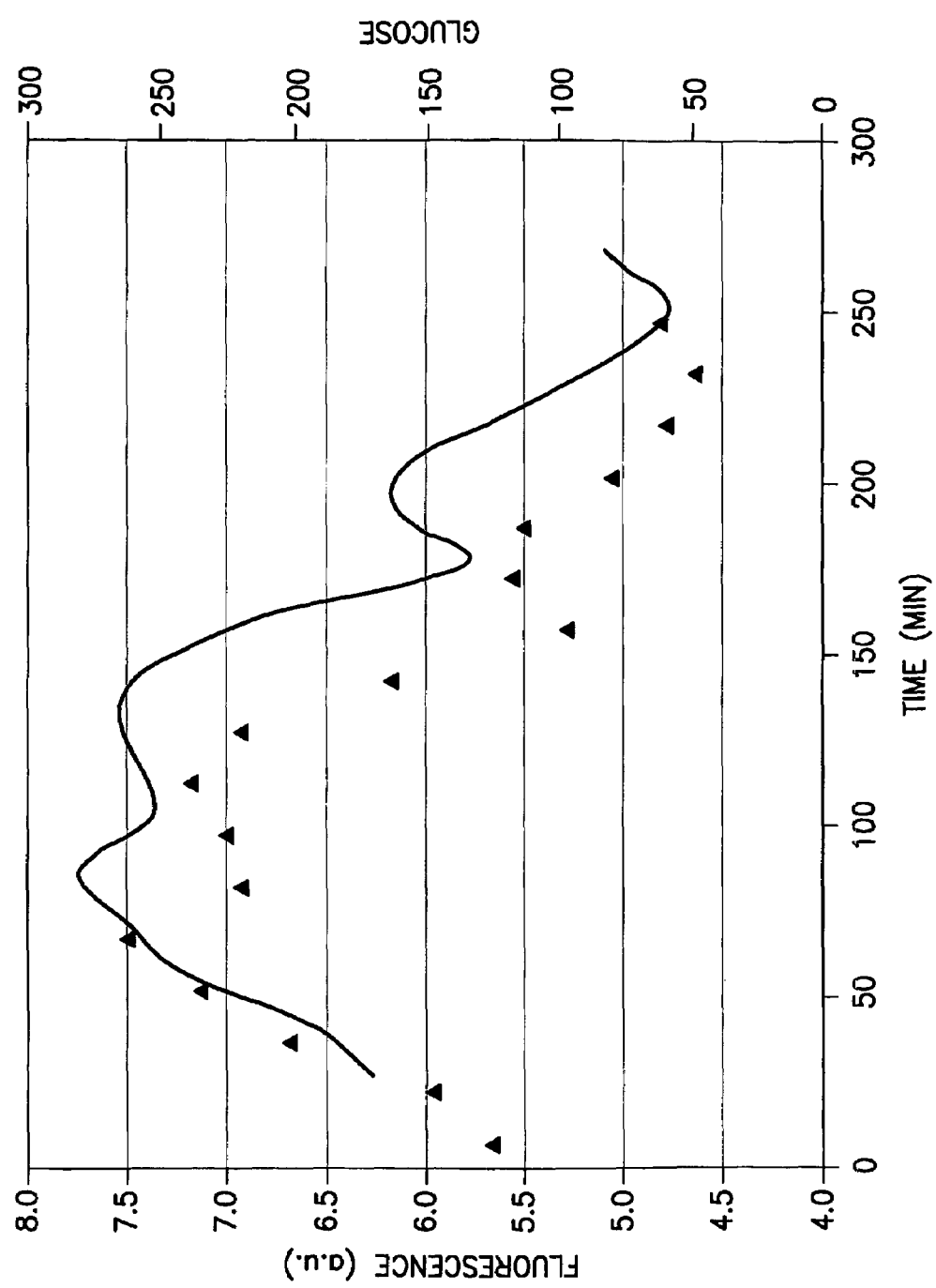
FIG. 11 is a chart showing the performance of an embodiment of a biosensor constructed in accordance with Example 7.

In a trial, the tip of the biosensor, including the needle, fiber, and sensing element, were inserted to an approximately 1-2 mm depth into the side of an awake diabetic Yukatan pig. The pig had been rendered diabetic via the administration of the drug streptozotozin. During the trial, the pig was alternately treated with insulin and food to adjust the glucose levels. At intervals, blood samples were taken through a throat catheter, and blood sugar readings were tested on a handheld blood glucose meter. The fluorescence intensity of the biosensor was observed to track changing glucose levels in the awake pig, as shown in FIG. 11. In FIG. 11, the solid curve represents the fluorescence signal from the biosensor, with units shown on the left hand y-axis. The triangles represent the blood glucose levels determined on the hand-held meter, with values read off the right-hand y-axis.

While the invention herein disclosed has been described by means of specific embodiments and applications thereof, numerous modifications and variations can be made thereto by those skilled in the art without departing from the scope of the invention as set forth in the claims.

What is claimed is:

1. A biosensor tip device for sensing glucose in a sample comprising:

at least one tip body having a proximal end and a distal end;

an optical fiber having a proximal end and a distal end; and a sensing element in optical proximity to the distal end of the tip body, the sensing element comprising at least one glucose galactose binding protein (GGBP), said GGBP being adapted to bind with at least glucose, and at least one reporter group associated with the GGBP, wherein the reporter group is adapted to undergo a luminescence change upon binding of the binding protein to the glucose, and wherein the sensing element is entrapped in or attached to a polymer matrix, wherein the polymeric matrix comprises reactive groups and the polymeric matrix is attached to the distal end of the optical fiber through amine groups that are on the surface of the optical fiber.

2. The device of claim 1, further comprising an optical coupling member configured and dimensioned to receive an attachable optical component thereto.

3. The device of claim 1, further comprising at least one reference group associated with the GGBP.

4. The device of claim 1, wherein said sensing element is further adapted to be inserted into or through the skin of a patient.

5. The device of claim 1, further comprising a temperature sensing element for sensing the temperature of the sample.

6. The device of claim 1, wherein at least one tip body further comprises one or more ports positioned between the proximal end and the distal end.

7. The device of claim 6, wherein the one or more ports is configured for delivery of a therapeutic agent therethrough.

8. The device of claim 1, wherein the tip body is a needle.

9. The needle assembly of claim 8, wherein the needle further comprises one or more ports positioned between the proximal end and the distal end.

10. The device of claim 8, wherein the needle comprises a bent tip portion that extends distally beyond and adjacent to the sensing element.

11. The device of claim 8, wherein the device comprises a plurality of tip bodies.

12. The device of claim 8, wherein the device comprises two tip bodies.

13. The device of claim 12, wherein the first of the two tip bodies comprises the sensing element, and the second of the two tip bodies comprises a delivery means for delivering the therapeutic agent to the patient.

14. The device of claim 13, wherein the sensing element is further attached to the inner surface of the first tip body via the polymeric matrix.

15. The device of claim 14, further comprising a mount.

16. The device of claim 8, wherein the sensing element is attached to the inner surface of the needle.

17. The device of claim 16, wherein the sensing element comprises a polymeric matrix and the sensing element is attached to the inner surface of the needle via the polymeric matrix.

18. The device of claim 17, wherein the polymeric matrix is further attached to the distal end of said optical fiber through reactive groups on said polymer.

19. The device of claim 18, wherein the reactive groups on the polymer bind to amine groups that are on the surface of the optical fiber.

20. The device of claim 19, wherein the needle comprises a bent tip portion that extends distally beyond and adjacent to the sensing element.

21. The device of claim 19, wherein the device comprises a plurality of tip bodies.

22. The device of claim 21, wherein the device comprises two tip bodies.

23. The device of claim 22, wherein the first of the two tip bodies comprises the sensing element, and the second of the two tip bodies comprises a delivery means for delivering the therapeutic agent to the patient.

24. The device of claim 23, further comprising a mount.

25. A method of detecting levels of glucose in a sample comprising
   a. acquiring access to said sample;
   b. inserting the device of claim 1 into said sample;
   c. allowing said sensing element to interact with said sample; and
   d. determining the extent of luminescence change of said reporter group,
   wherein the extent of luminescence change is indicative of the levels of said glucose in said sample.

26. The method of claim 25 wherein the sample is selected from the group consisting of blood, plasma, serum and interstitial fluid.

27. The method of claim 26, wherein the sample is blood.

28. The method of claim 27, wherein said sample is in vitro.

29. The method of claim 27, wherein said sample is in vivo.

30. The method of claim 29, further comprising accessing said sample through the skin of said subject.

31. The method of claim 30, wherein said sample is accessed subcutaneously.

32. The method of claim 30, wherein said sample is accessed intradermally.

33. The method of claim 30, wherein said sample is accessed using a needle.

34. The method of claim 30, wherein said sensing element is placed directly into said sample, without removing said sample from said subject.

35. The method of claim 30, wherein a portion of said sample is removed from said subject prior to placing said sensing element into said sample.

* * * * *